(12) United States Patent
Belef et al.

(10) Patent No.: US 6,942,674 B2
(45) Date of Patent: Sep. 13, 2005

(54) APPARATUS AND METHODS FOR DELIVERING A CLOSURE DEVICE

(75) Inventors: W. Martin Belef, San Jose, CA (US); William N. Aldrich, Napa, CA (US); Michael T. Carley, San Jose, CA (US); Ronald J. Jabba, Redwood City, CA (US); Stephen M. Salmon, Napa, CA (US); Anthony Pantages, Los Altos, CA (US); Javier Sagastegui, Castro Valley, CA (US)

(73) Assignee: Integrated Vascular Systems, Inc., Sunnyvale, CA (US)

( * ) Notice: Subject to any disclaimer, the term of this patent is extended or adjusted under 35 U.S.C. 154(b) by 398 days.

(21) Appl. No.: 10/081,723

(22) Filed: Feb. 21, 2002

(65) Prior Publication Data

US 2002/0193808 A1 Dec. 19, 2002

Related U.S. Application Data

(63) Continuation-in-part of application No. 09/732,835, filed on Dec. 7, 2000, now Pat. No. 6,780,197, which is a continuation-in-part of application No. 09/610,238, filed on Jul. 5, 2000, now Pat. No. 6,391,048, which is a continuation-in-part of application No. 09/478,179, filed on Jan. 5, 2000, now Pat. No. 6,197,042.

(51) Int. Cl.[7] ............................................. A61B 17/10
(52) U.S. Cl. ....................... 606/142; 606/213; 606/139
(58) Field of Search ..................... 606/1, 108, 138–158, 606/185, 190–198, 213–221; 604/104–109

(56) References Cited

U.S. PATENT DOCUMENTS

| 3,586,002 A | 6/1971 | Wood |
| 3,604,425 A | 9/1971 | LeRoy |
| 3,677,243 A | 7/1972 | Nerz |
| 3,757,629 A | 9/1973 | Schneider |
| 3,805,337 A | 4/1974 | Branstetter |

(Continued)

FOREIGN PATENT DOCUMENTS

WO    WO 01/35832 A2    5/2001

OTHER PUBLICATIONS

PCT Publication No. WO 00/07640, "Vascular Suction Cannula, Dialator and Surgical Stapler", Feb. 17, 2000.
PCT Publication No. WO 00/56227, entitled "Advanced Closure Device", Sep. 28, 2000.
PCT Publication No. WO 00/56223 entitled "Vascular Closure Device", Sep. 28, 2000.
PCT Publication No. WO 99/62408 entitled "Vascular Port Device", Dec. 9, 1999.
PCT Publication No. WO 98/24374, "Vascular Wound Closure System", Yong Zhu, et al., Jun. 11, 1998.
PCT Publication No. WO 97/20505, "Vascular Wound Closure Device", Yong Zhu, et al., Jun. 12, 1997.

*Primary Examiner*—Glenn K. Dawson
(74) *Attorney, Agent, or Firm*—Orrick Herrington & Sutcliffe, LLP

(57) ABSTRACT

An apparatus for delivering a clip to close an opening through tissue includes a sheath and a carrier assembly including a clip therein that is slidable on the sheath. An actuator assembly is connectable to the sheath, and telescoping actuator members extend from the handle that are connectable to the carrier assembly for advancing the carrier assembly along the sheath. An obturator on the actuator assembly includes splines that may be deployed beyond a distal end of the sheath, and expanded to a transverse expanded configuration for positioning the sheath before deploying the clip. The actuator members include cooperating detents that selectively release the actuator members as the carrier assembly reaches predetermined positions along the sheath for deploying the clip from the carrier assembly, and that collapse the splines to allow removal of the apparatus after deploying the clip.

42 Claims, 14 Drawing Sheets

U.S. PATENT DOCUMENTS

| | | | |
|---|---|---|---|
| 4,192,315 A | 3/1980 | Hilzinger et al. | |
| 4,217,902 A | 8/1980 | March | |
| 4,345,606 A | 8/1982 | Littleford | |
| 4,396,139 A | 8/1983 | Hall et al. | |
| 4,411,654 A | 10/1983 | Boarini et al. | |
| 4,412,832 A | 11/1983 | Kling et al. | |
| 4,485,816 A | 12/1984 | Krumme | |
| RE31,855 E | 3/1985 | Osborn | |
| 4,505,274 A | 3/1985 | Speelman | |
| 4,586,503 A | 5/1986 | Kirsch et al. | |
| 4,687,469 A | 8/1987 | Osypka | |
| 4,772,266 A | 9/1988 | Groshong | |
| 4,777,950 A | 10/1988 | Kees, Jr. | |
| 4,860,746 A | 8/1989 | Yoon | |
| 4,865,026 A | 9/1989 | Barrett | |
| 4,917,087 A | 4/1990 | Walsh et al. | |
| 4,950,258 A | 8/1990 | Kawai et al. | |
| 5,007,921 A | 4/1991 | Brown | |
| 5,026,390 A | 6/1991 | Brown | |
| 5,053,008 A | 10/1991 | Bajaj | |
| 5,108,420 A | 4/1992 | Marks | |
| 5,156,609 A | 10/1992 | Nakao et al. | |
| 5,167,634 A | 12/1992 | Corrigan, Jr. et al. | |
| 5,176,648 A | 1/1993 | Holmes et al. | |
| 5,192,302 A | 3/1993 | Kensey et al. | |
| 5,222,974 A | 6/1993 | Kensey et al. | |
| 5,275,616 A | 1/1994 | Fowler | |
| 5,304,184 A | 4/1994 | Hathaway et al. | |
| 5,318,542 A | 6/1994 | Hirsch et al. | |
| 5,334,217 A | 8/1994 | Das | |
| 5,366,458 A | 11/1994 | Korthoff et al. | |
| 5,478,354 A | 12/1995 | Tovey et al. | |
| 5,527,322 A | 6/1996 | Klein et al. | |
| 5,674,231 A * | 10/1997 | Green et al. | 606/142 |
| 5,683,405 A | 11/1997 | Yacoubian et al. | |
| 5,695,505 A | 12/1997 | Yoon | |
| 5,728,114 A | 3/1998 | Evans et al. | |
| 5,782,844 A | 7/1998 | Yoon et al. | |
| 5,782,860 A | 7/1998 | Epstein et al. | |
| 5,782,861 A | 7/1998 | Cragg et al. | |
| 5,810,846 A | 9/1998 | Virnich et al. | |
| 5,810,851 A | 9/1998 | Yoon | |
| 5,817,113 A | 10/1998 | Gifford | |
| 5,820,631 A | 10/1998 | Nobles | |
| 5,830,125 A | 11/1998 | Scribner et al. | |
| 5,879,366 A | 3/1999 | Shaw et al. | |
| 5,910,155 A * | 6/1999 | Ratcliff et al. | 606/213 |
| 5,922,009 A | 7/1999 | Epstein et al. | |
| 5,951,518 A | 9/1999 | Licata et al. | |
| 5,951,589 A | 9/1999 | Epstein et al. | |
| 5,964,782 A | 10/1999 | LaFontaine et al. | |
| 5,984,934 A | 11/1999 | Ashby et al. | |
| 6,007,563 A | 12/1999 | Nash et al. | |
| 6,036,720 A | 3/2000 | Abrams et al. | |
| 6,045,570 A | 4/2000 | Epstein et al. | |
| 6,056,769 A | 5/2000 | Epstein et al. | |
| 6,056,770 A | 5/2000 | Epstein et al. | |
| 6,063,085 A | 5/2000 | Tay et al. | |
| 6,077,281 A | 6/2000 | Das | |
| 6,077,291 A | 6/2000 | Das | |
| 6,080,182 A | 6/2000 | Shaw | |
| 6,080,183 A | 6/2000 | Tsugita et al. | |
| 6,120,524 A | 9/2000 | Taheri | |
| 6,197,042 B1 * | 3/2001 | Ginn et al. | 606/213 |
| 6,348,064 B1 | 2/2002 | Kanner | |
| 6,695,867 B2 * | 2/2004 | Ginn et al. | 606/213 |
| 2003/0009180 A1 | 1/2003 | Hinchliffe et al. | |
| 2003/0093096 A1 | 5/2003 | McGuckin et al. | |

* cited by examiner

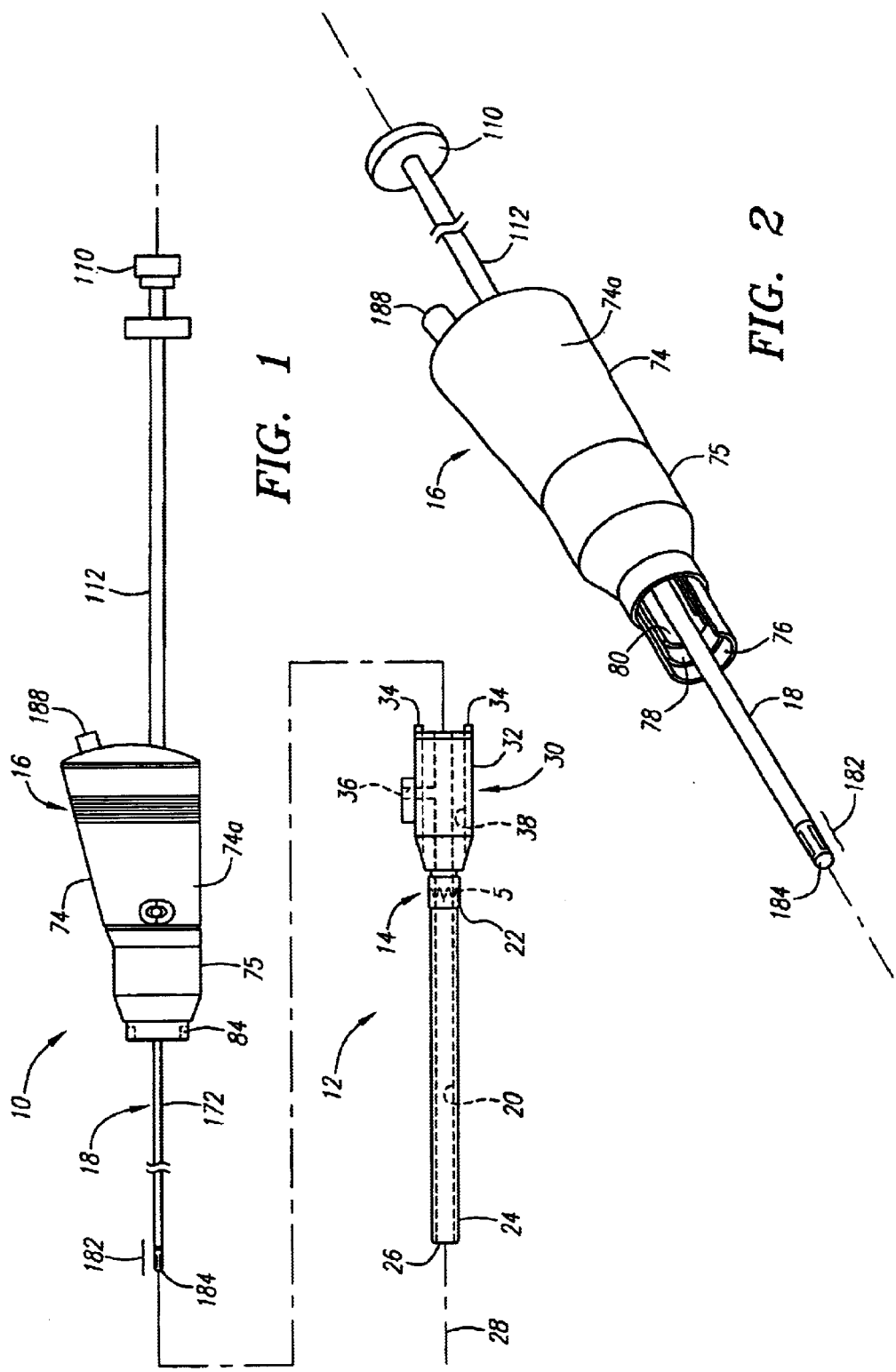

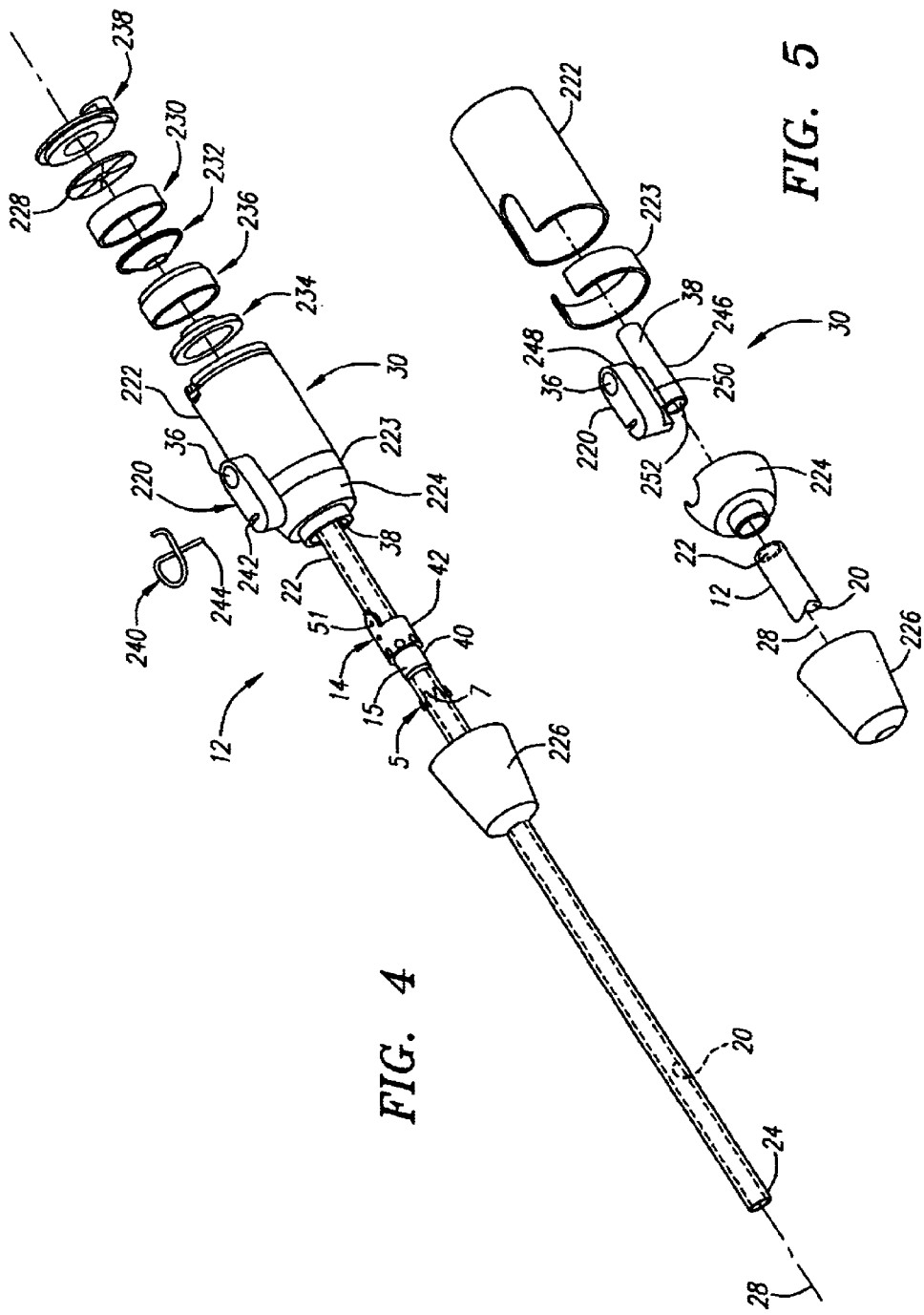

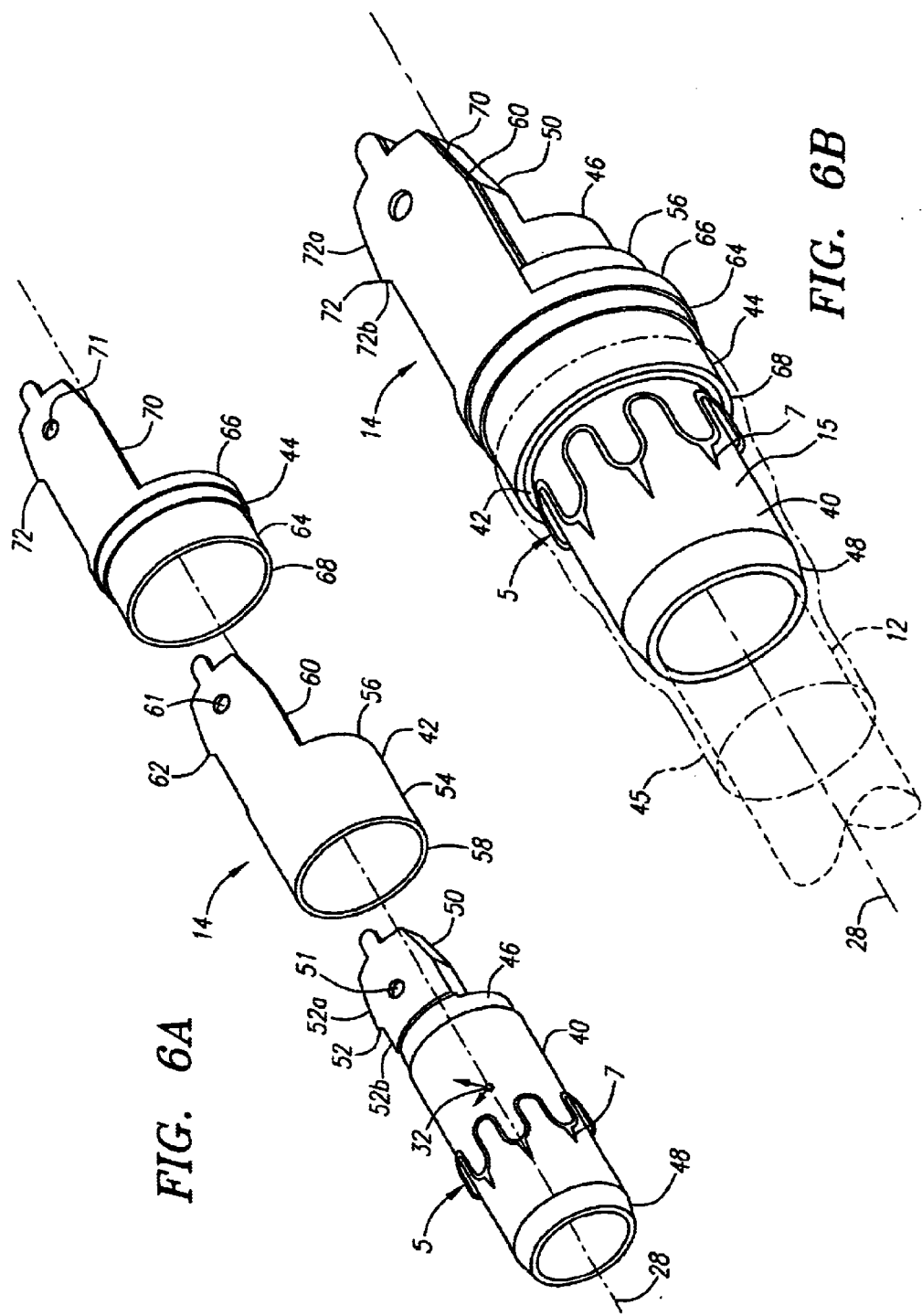

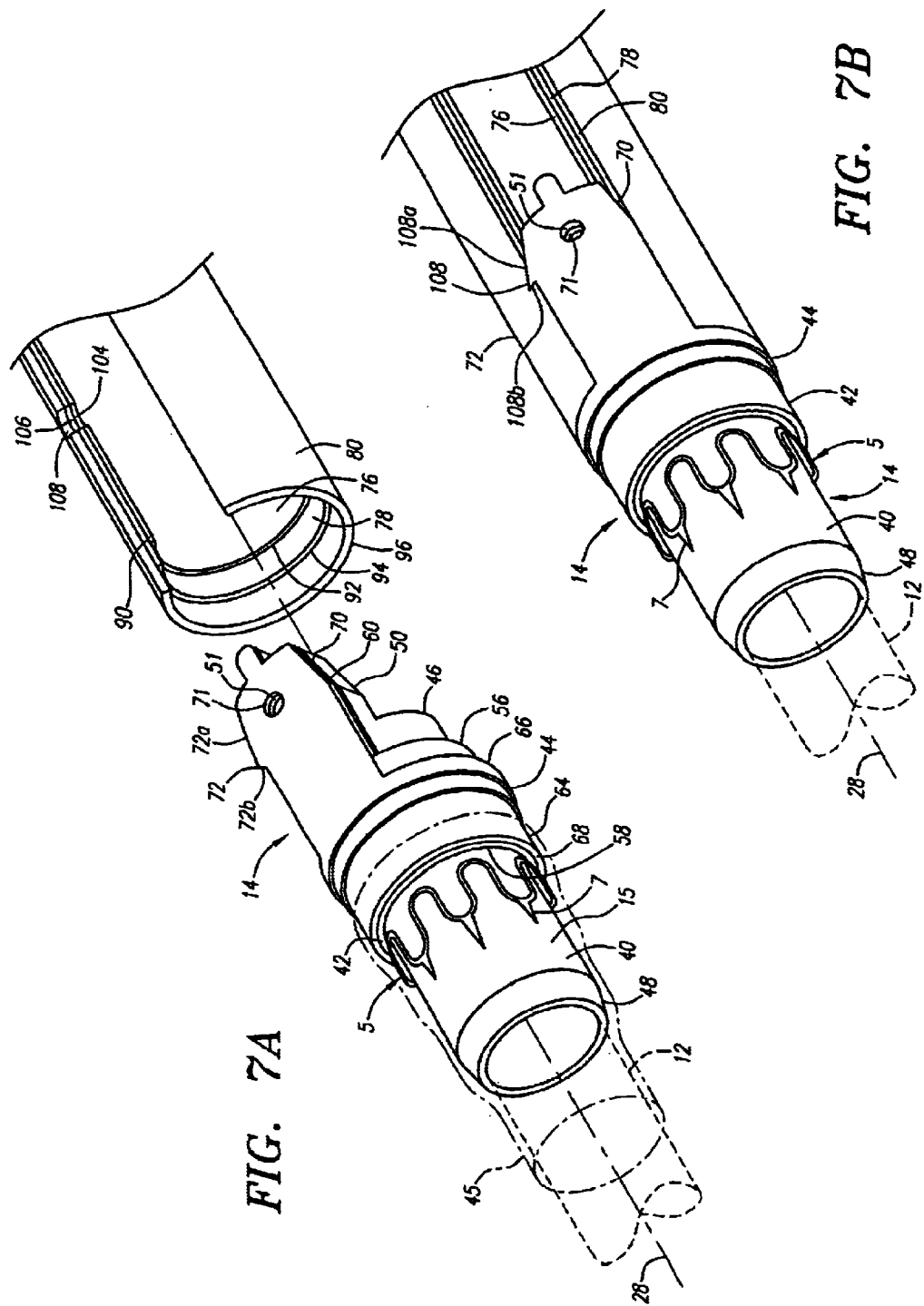

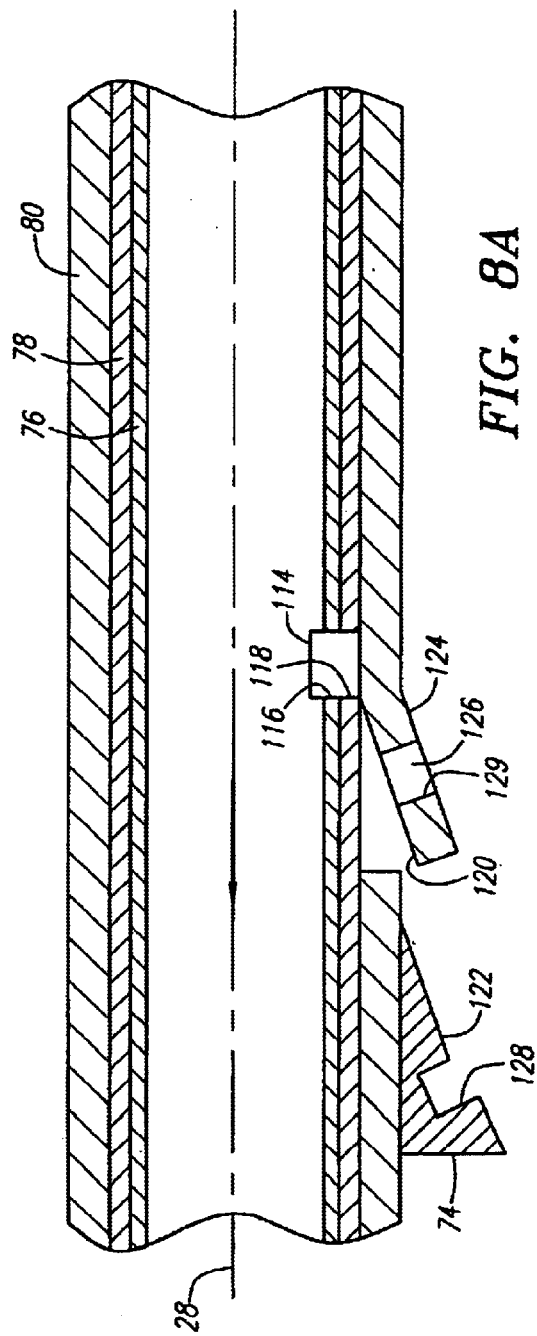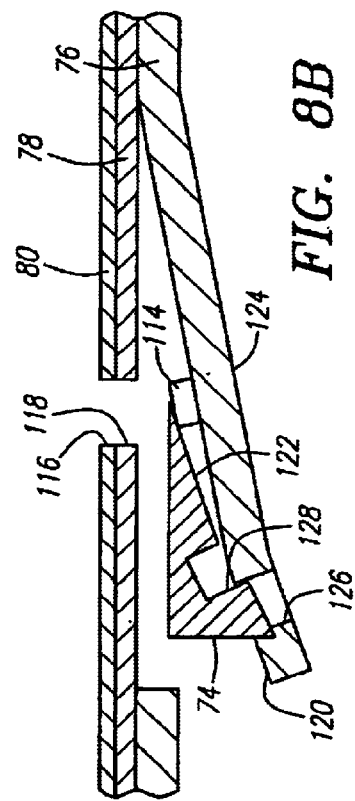

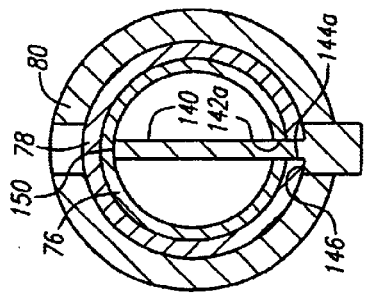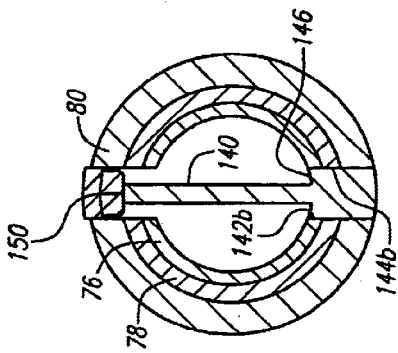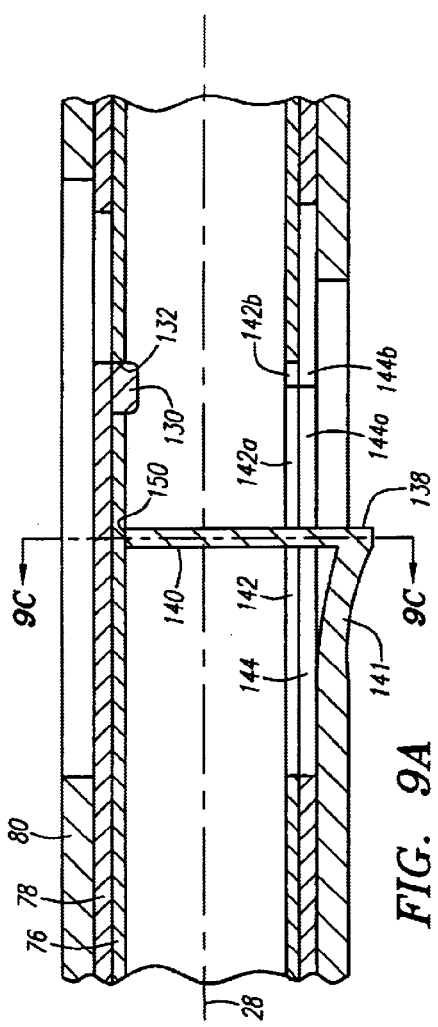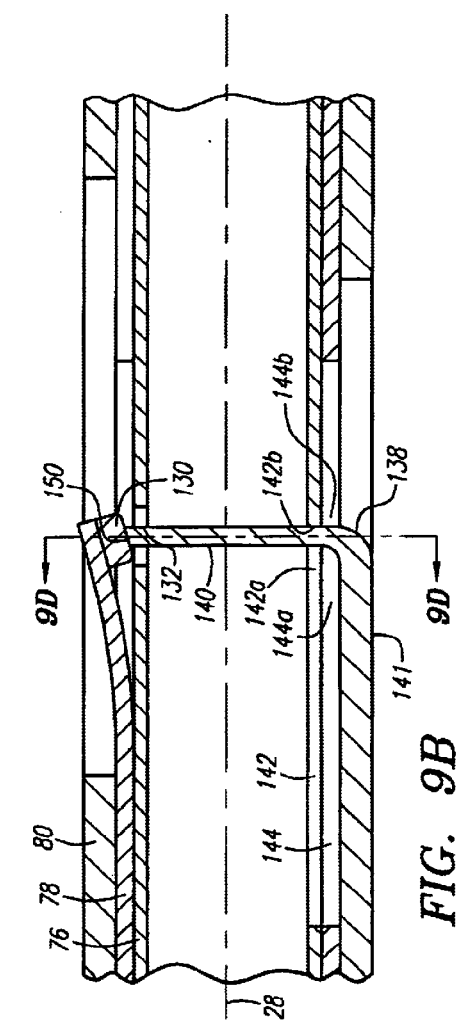

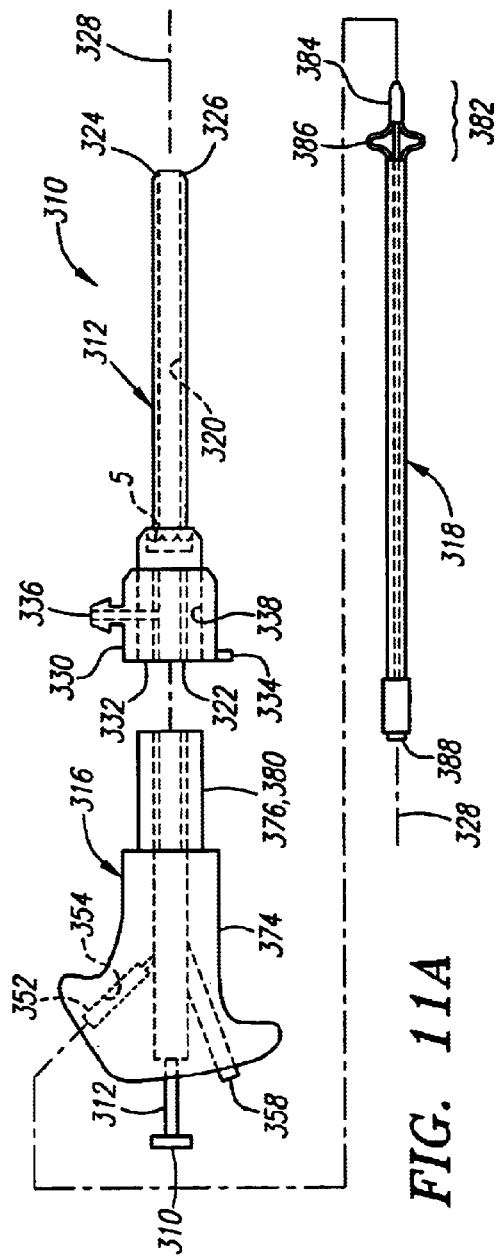
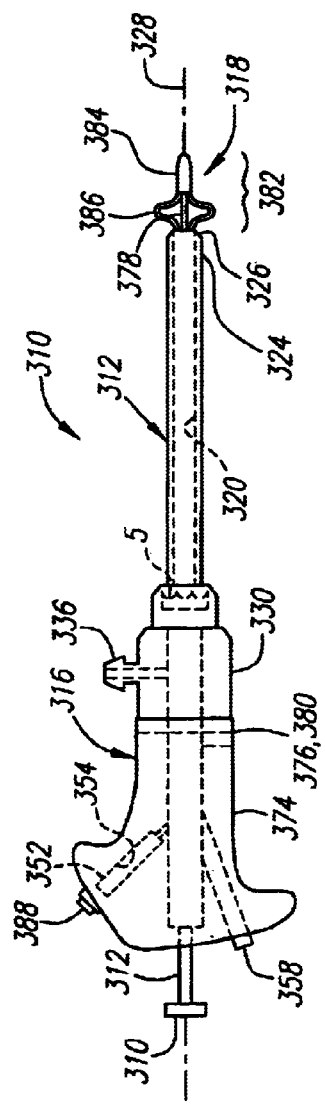
FIG. 11A
FIG. 11B

APPARATUS AND METHODS FOR DELIVERING A CLOSURE DEVICE

This application is a continuation-in-part of application Ser. No. 09/732,835, filed Dec. 7, 2000 now U.S. Pat. No. 6,780,197, which is a continuation-in-part of application Ser. No. 09/610,238, filed Jul. 5, 2000 now U.S. Pat. No. 6,391,048, which is a continuation-in-part of application Ser. No. 09/478,179, filed Jan. 5, 2000, now U.S. Pat. No. 6,197,042, the disclosures of which are expressly incorporated herein by reference.

FIELD OF THE INVENTION

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure.

BACKGROUND

Catheterization and interventional procedures, such as angioplasty or stenting, generally are performed by inserting a hollow needle through a patient's skin and tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

To facilitate positioning devices that are percutaneously inserted into a blood vessel, "bleed back" indicators have been suggested. For example, U.S. Pat. No. 4,317,445, issued to Robinson, discloses a flashback chamber on a first end of a cannula that communicates with a port on a second end. The second end is percutaneously introduced into a patient until the port enters the vessel, whereupon blood, under normal blood pressure, may advance along the cannula and enter the flashback chamber, thereby providing a visual indication that the vessel has been entered. This reference, however, does not discuss vascular wound closure, but is merely directed to an introducer device. In contrast, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel. The loop may also provide a support for facilitating deploying and deflecting a surgical clip against the vessel wall. Such a device, however, may risk engagement between the loop and the surgical clip, thereby preventing the loop from being withdrawn from the vessel.

Accordingly, apparatus and methods for delivering a device for closing a vascular puncture site or other opening through tissue would be useful.

SUMMARY OF THE INVENTION

The present invention is directed to apparatus and methods for closing and/or sealing openings through tissue, e.g., into body lumens, and more particularly to apparatus and methods for delivering a vascular closure element for closing a puncture in a blood vessel formed during a diagnostic or therapeutic procedure, e.g., when an introducer sheath is advanced into the vessel.

In accordance with one aspect of the present invention, an apparatus is provided for delivering a closure element or other annular-shaped device into an opening through tissue, e.g., for engaging tissue adjacent to the opening to close and/or seal the opening. The apparatus includes an elongate member including proximal and distal ends, such as an introducer sheath that includes a lumen for advancing one or more devices into a body lumen during a procedure.

A carrier assembly is slidable on the elongate member, the carrier assembly including an inner carrier member, a middle pusher member, and, optionally, an outer skin, nested together. Each member may have an annular shape, and may include a connector on its proximal end. The pusher member may be disposed about the carrier member to define a space distal to the pusher member along an outer surface of the carrier member. The outer skin has a length, whereby the outer skin may extend over the space and/or contact an outer surface of the elongate member. In a preferred embodiment, the outer skin extends a short distance beyond a distal end of the carrier member, such that the outer skin is slidable along the elongate member.

An annular-shaped element, e.g., a clip or other closure device, may be received on the carrier member within the space, the annular-shaped element being deployable from the space upon distal movement of the pusher member relative to the carrier member.

In addition, the apparatus may include an actuator assembly including a housing and inner, intermediate, and outer actuator members that telescope relative to the housing and/or to each other. The housing may be connectable to the proximal end of the elongate member, e.g., to a hub on the proximal end by cooperating connectors on the hub and the housing. Each actuator member may include a connector on its distal end for engaging a respective member of the carrier assembly, thereby coupling movement of the carrier, pusher, and sheath members to the inner, intermediate, and outer actuator members, respectively. If the outer skin is eliminated from the carrier assembly, the outer actuator member may be eliminated from the actuator assembly.

In a preferred embodiment, the actuator assembly includes a control member that is coupled to one or more of the actuator members, preferably, but not necessarily, the intermediate actuator member. The inner, intermediate, and outer actuator members may include cooperating detents for coupling distal movement of the inner, intermediate, and outer actuator members together in a predetermined manner as the control member is directed distally.

For example, a first set of cooperating detents may be provided that initially couples the inner, intermediate, and outer actuator members together, and releases the outer actuator member upon attaining a first distal position. The inner and intermediate actuator members may be directed distally further, consequently permitting the carrier and/or pusher members to be directed distally relative to the outer skin. In an exemplary embodiment, the first set of cooperating detents may include a first detent on the outer tubular member and first pockets in the inner and intermediate tubular members for receiving the first detent therein. Cooperating ramps may be provided on the outer tubular member that are configured for disengaging the first detent from the first pockets upon attaining the first distal position, thereby allowing the inner and intermediate tubular members to be directed distally beyond the first distal position.

In addition, the cooperating detents may include a second set of cooperating detents on the inner and intermediate actuator members for coupling movement of the inner and intermediate actuator members together to a second distal position distal to the first distal position. For example, the intermediate actuator member may include a second detent, and the inner actuator member may include a second pocket for receiving the second detent therein. The housing or the outer actuator member may include a spring element for disengaging the second detent from the second pocket upon attaining the second distal position. For example, the spring element may include a beam extending from the outer tubular member through slots in the inner and intermediate tubular members, the beam being received in the second pocket upon attaining the second distal position, thereby disengaging the second detent and allowing further distal movement of the intermediate member while substantially simultaneously coupling the inner and outer tubular members together.

The intermediate actuator member may be advanced distally beyond the second distal position by directing the control member further distally, thereby directing the pusher member distally with respect to the carrier member to deploy the annular-shaped element from the space.

In addition, the actuator assembly may also include an obturator or locator member that may be part of the actuator assembly or may be connected to the actuator assembly. A distal portion of the locator member may extend distally beyond the actuator members. In addition, the locator member has sufficient length such that the distal portion may extend beyond the distal end of the elongate member when the actuator assembly is connected to the elongate member. One or more positioning elements on the distal portion of the locator member may be movable from a collapsed configuration towards a transversely expanded configuration. A locking mechanism on the locator member and/or actuator assembly may releasably retain the positioning elements in the expanded configuration.

In a preferred embodiment, the locator member is substantially permanently attached to the actuator assembly such that the distal portion extends through and beyond the inner actuator member. Alternatively, the actuator assembly may include a tubular portion or recess communicating via an interior of the inner actuator member with a lumen of the elongate member. In this embodiment, the locator member may be inserted into the tubular portion until the positioning elements are disposed beyond the distal end of the elongate member. One of the inner, intermediate, and outer actuator members may include a third detent for engaging a release mechanism for disengaging the locking mechanism on the locator member. Thus, the positioning elements may be collapsed to the collapsed configuration upon advancing one of the inner, intermediate, and/or outer actuator members, preferably the intermediate actuator member, to its final distal position.

Other objects and features of the present invention will become apparent from consideration of the following description taken in conjunction with the accompanying drawings.

BRIEF DESCRIPTION OF THE DRAWINGS

FIG. 1 is an exploded side view of a first preferred embodiment of an apparatus for delivering a closure element, including an introducer sheath, and an actuator assembly, in accordance with the present invention.

FIG. 2 is a perspective view of the actuator assembly for the apparatus of FIG. 1.

FIG. 4 is a partially exploded perspective view of the introducer sheath shown in FIGS. 1 and 3A.

FIG. 5 is an exploded perspective view of a hub assembly of the introducer sheath shown in FIG. 4.

FIG. 6A is an exploded perspective view of a carrier assembly, including a carrier member, a pusher member, and an anchor member, for use with the apparatus of FIGS. 1–5.

FIG. 6B is a perspective view of the carrier assembly of FIG. 6A, with the carrier, pusher, and anchor members assembled substantially coaxially with respect to one another.

FIGS. 7A and 7B are perspective views of the carrier assembly of FIGS. 6A and 6B aligned with and attached to a distal end of the actuator assembly of FIG. 1, respectively.

FIGS. 8A and 8B are cross-sectional details of telescoping tubular members of the actuator assembly of FIGS. 1–3, showing cooperating detents for releasably coupling an outer tubular member to inner and intermediate tubular members.

FIGS. 9A–9D are cross-sectional details of the telescoping tubular members of FIGS. 8A and 8B, showing cooperating detents for releasably coupling the inner and intermediate tubular members.

FIGS. 11A and 11B are side views of a second preferred embodiment of an apparatus for delivering a closure element, in accordance with the present invention.

DETAILED DESCRIPTION OF THE PREFERRED EMBODIMENTS

Figures 3A, 3B:
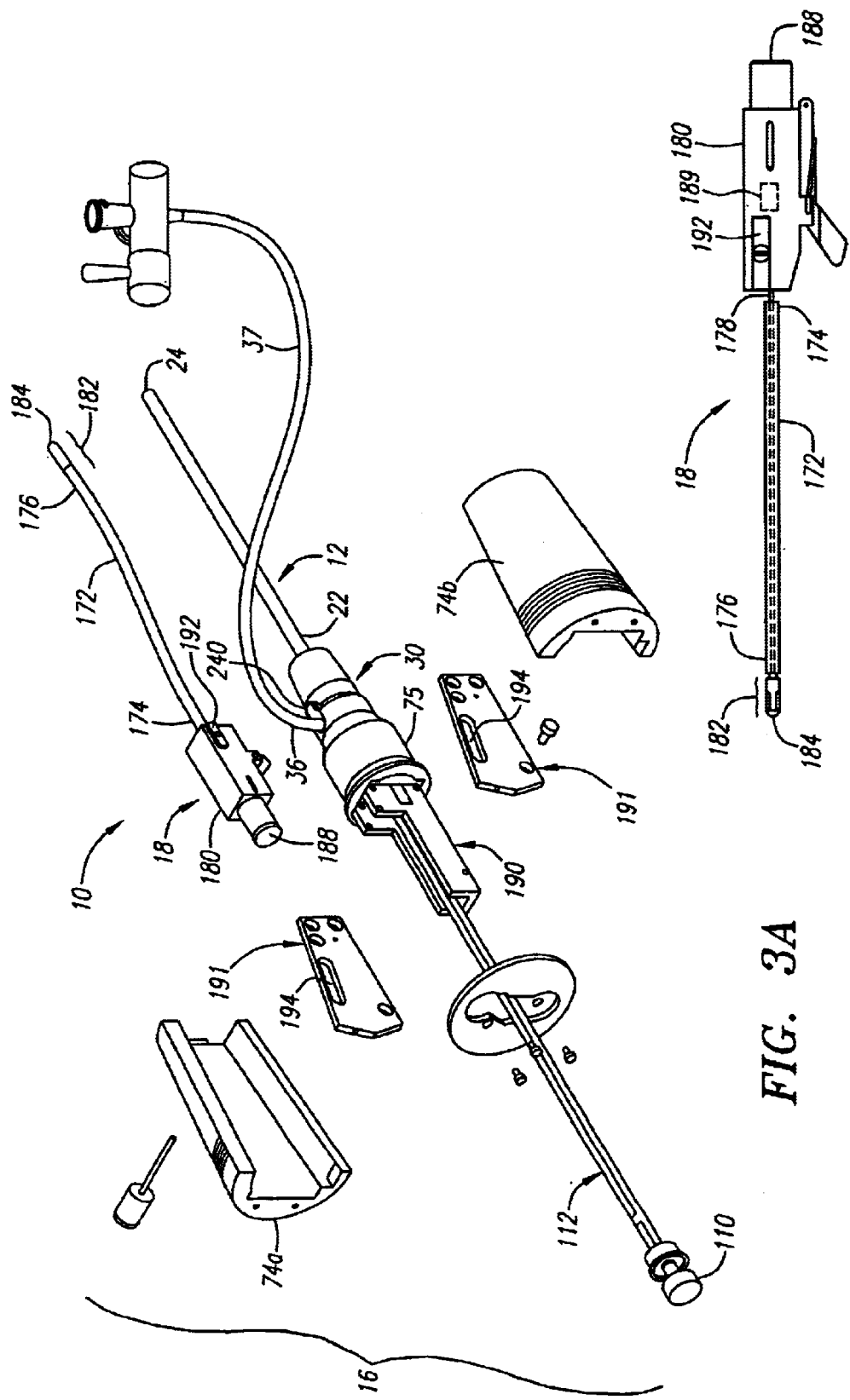
FIG. 3A is an exploded perspective view of the apparatus of FIG. 1.
FIG. 3B is a side of view of an obturator assembly for the actuator assembly of FIGS. 1–3A.

Turning to the drawings, FIGS. 1–4 show a first preferred embodiment of an apparatus 10 for delivering a closure element, such as a clip 5 (shown in phantom), into an opening through tissue for closing the opening (not shown). Generally, the apparatus 10 includes an introducer sheath 12, a housing or carrier assembly 14 slidably disposed on the sheath 12, and an actuator or actuator assembly 16 that is connectable to the introducer sheath 12. In addition, the apparatus 10 may also include a locator member or obturator 18, which may be part of the actuator assembly 16, as shown in FIGS. 1–3. Alternatively, the apparatus 310 may include an obturator 318 that is a separate subassembly that may be inserted through an actuator assembly 316 and/or sheath 312, as shown in FIGS. 11A and 11B.

As best seen in FIGS. 1 and 4, the introducer sheath 12 is generally a substantially flexible or semi-rigid tubular member including a lumen 20 extending along a longitudinal axis 28 between its proximal and distal ends 22, 24. The distal end 24 has a size and shape to facilitate insertion into an opening through tissue (not shown), e.g., having a tapered tip 26 for facilitating substantially atraumatic introduction through a passage and/or at least partially into a blood vessel or other body lumen accessed via the passage. The lumen 20 has a size for accommodating insertion of one or more devices therethrough, such as a catheter, guidewire, and the like (not shown).

Returning to FIGS. 1, 4, and 5, a hub assembly 30 is attached to the proximal end 22 of the sheath 12, e.g., by an adhesive, cooperating connectors, and/or a thermomechanical joint. Thus, the hub assembly 30 and the sheath 12 may define a passage 38 (see FIG. 1) therebetween that extends substantially parallel to the longitudinal axis 28. The hub assembly 30 may include a keel member 220 and one or more outer annular bodies 222–226 that may be attached to one another, e.g., using butt or lap joints secured with adhesives, mechanical connectors, and the like.

For example, the hub assembly 30 may include a rear main body 222, a spacer 223, a nose ring 224, and a strain relief forward nose 226 that may be substantially permanently attached to one another. The keel member 220 may include a tubular portion 246, and a shoulder portion 248 connected by a radial spoke 250 that may extend transversely with respect to the longitudinal axis 28. The proximal end 22 of the sheath 12 may be connected to the tubular portion 246 such that a passage 252 through the tubular portion 246 communicates with the lumen 20. The main body 222 and nose ring 224 may be connected to the shoulder portion 248 such that an annular passage 38 may be defined between the tubular portion 246 and the main body 222 and nose ring 224. The passage 38 may have a "C" shape along the portion of the hub assembly 30 through which the spoke 248 of the keel member 220 extends.

With particular reference to FIG. 4, the hub assembly 30 may also include one or more seals and/or valves that provide a fluid-tight seal. Thus, one or more devices, such as the obturator 18 (not shown in FIG. 4), may be inserted into the lumen 20 of the sheath 12 without fluid passing proximally through the lumen 20. For example, the hub assembly 30 may include a thrust washer and/or valve 228, a valve 230, a guide 232 for directing devices into the lumen 20 of the sheath 12, and a seal 234. The various seals and/or guides may be secured to the hub assembly 30 by a spacer 236 and/or an end cap 238.

In addition, the hub assembly 30 may include one or more connectors on its proximal end 32, such as tabs 34 (see FIG. 1) and/or recesses or pockets (not shown) for cooperating with mating connectors on the actuator assembly 16, as described further below. Optionally, the hub assembly 30 may also include a side port 36 that extends from the shoulder portion 248 to the passage 252, thereby communicating with the lumen 20. The side port 36 may communicate with tubing 37 (see FIG. 3A), for example, to infuse fluids into the lumen 20 through the sheath 12. Alternatively, or in addition, the side port 36 may provide a "bleed back" indicator, such as that disclosed in application Ser. No. 09/680,837, filed Oct. 6, 2000, which is assigned to the assignee of the present invention. The disclosure of this application and any references cited therein are expressly incorporated herein by reference.

Returning to FIG. 4, the carrier assembly 14 is slidably disposed on an exterior of the sheath 12 and is configured for releasably holding the clip 5. The carrier assembly 14 is preferably slidable from a proximal position, e.g., near, adjacent to, or at least partially disposed within the passage 38, to one or more distal positions towards the distal end 24 of the sheath 12, as explained further below. Optionally, the hub assembly 30 may include a carrier release pin 240 that may be inserted into a hole, slot, or other aperture 242 in the shoulder portion 248. An inner tip 244 of the pin 240 may be received in one or more corresponding holes 51, 61, 71 (best seen in FIG. 6A) in the carrier assembly 14. The pin 240 may provide a safety feature, e.g., preventing premature advancement of the carrier assembly 14 and/or deployment of the clip 5, and/or may assist in aligning the carrier assembly 14 as will be appreciated by those skilled in the art.

As best seen in FIGS. 6A and 6B, the carrier assembly 14 may include an inner carrier member 40, a middle pusher member 42, and an outer anchor member 44 that may be nested together and coaxially disposed around the sheath 12 (shown in phantom in FIG. 6B). The carrier member 40 is an annular-shaped body 32 including proximal and distal ends 46, 48. As used herein, an "annular-shaped body" or "annular body" (whether referring to the carrier assembly 14 or the clip 5) includes any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis.

A tongue 50 may extend proximally from the proximal end 46 substantially parallel to the longitudinal axis 28. The tongue 50 may include a tab 52 or other connector, having a ramped proximal edge 52a and a substantially blunt distal edge 52b, for coupling movement of the carrier member 40 to the actuator assembly 16, as described further below. The distal end 48 of the carrier member 40 may be tapered or otherwise configured for facilitating substantially atraumatic advancement of the carrier member 40 through tissue, also as described further below.

The pusher member 42 is also an annular body 54, including proximal and distal ends 56, 58 and a tongue 60 extending from the proximal end 56 having a tab 62 thereon. The pusher member 42 is configured to slidably fit around the carrier member 40, but has a substantially shorter length than the carrier member 40. Thus, the carrier and pusher members 40, 42 may at least partially define a space 15 distal to the distal end 58 of the pusher member 42 and along an outer surface of the carrier member 40.

The anchor member or ring 44 may also be an annular body 64, including proximal and distal ends 66, 68 and a tongue 70 extending from the proximal end 66 having a tab 72 thereon, similar to the carrier and pusher members 40, 42. The anchor member 44 preferably includes an outer skin or sleeve 45 (shown in phantom in FIG. 6B) attached to and extending distally from the distal end 68 of the anchor ring 44, thereby extending over the space 15 to define a space (not shown). For example, the outer sleeve 45 may be lapped over and/or bonded to the anchor member 44.

The outer sleeve 45 may be formed from a substantially flexible material, which may be inelastic or elastic, and/or may include a substantially slippery outer surface. Exemplary materials include polytetrafluoroethylene (PTFE), polyethylene terephthalate (PET) or other polyester, latex, silicone, polyamides, polyurethanes, and/or blends or copolymers thereof. The outer sleeve 45 may have a length that is substantially longer than the carrier member 40 such that the outer sleeve 45 extends beyond the distal end 48 of the carrier member 40. For example, the outer sleeve 45 may extend up to fifteen millimeters (15 mm) or more beyond the carrier member 40 and/or may slidably surround the sheath 12. The outer sleeve 45 may protect the clip 5 or tissue through which the carrier assembly 14 is advanced, and/or may facilitate advancing the carrier assembly 14 through multiple layers of tissue, as explained further below.

Figure 6C:
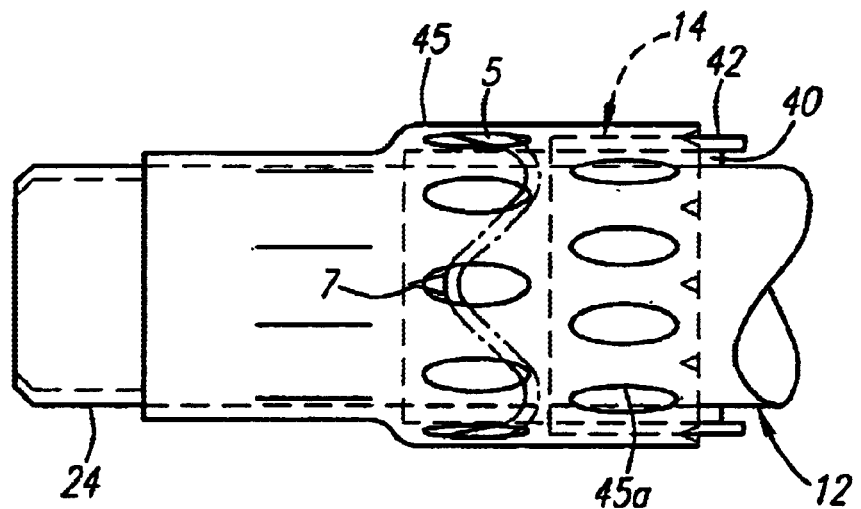
FIG. 6C is a side view of the carrier assembly of FIGS. 6A and 6B, showing slots in an outer sleeve expanding to accommodate advancing the carrier and pusher members relative to the anchor member.
Figure 6D:
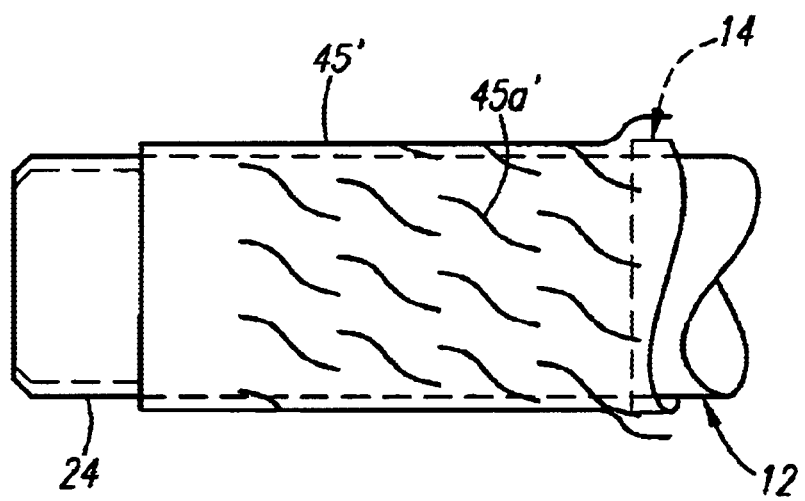
FIG. 6D is a side view of an alternative embodiment of the carrier assembly of FIG. 6C, showing spiral slots in the outer sleeve.

Optionally, the outer sleeve 45 may include weakened regions, e.g., longitudinal slots or perforations 45a or thin walled regions (not shown), that may be torn, expanded, and/or enlarged during advancement of the carrier and pusher members 40, 42 relative to the outer sleeve 34, as explained further below. For example, the outer sleeve 45 may include a plurality of longitudinal slots 45a with circumferentially adjacent slots being staggered longitudinally from one another, as shown in FIG. 6C. This slot arrangement may facilitate the outer sleeve 45 expanding or being deflected out of the way upon advancing the carrier and pusher members 40, 42 without fully exposing the clip 5, as explained further below. Alternatively, as shown in FIG. 6D, the longitudinal slots may be spiral slots 45a' formed in the outer sleeve 45,' Spiral slots 45a' may minimize tissue moving as the carrier assembly 14 is advanced through tissue (not shown), as described further below.

In a further alternative, a substantially flexible sleeve or skin (not shown) may be provided that extends over the space 15, similar to the outer sleeve 45, but that may be bonded or otherwise secured to the outer surface of the introducer sheath 12. Embodiments of such a skin may be found in co-pending application Ser. No. 10/081,725, now U.S. Pat. No. 6,749,621, filed on the same day as the present application and entitled "Sheath Apparatus and Methods for Delivering a Closure Device," which is assigned to the assignee of the present application. The disclosure of this application and any references cited therein are expressly incorporated herein by reference. The disclosure of this application and any references cited therein are expressly incorporated herein by reference. In yet another alternative, it may be possible to eliminate the anchor member 44 and/or the outer sleeve 45 completely, such that the clip 5 remains exposed on the carrier member 40.

In a preferred embodiment, the carrier, pusher, and anchor members 40, 42, 44 are coaxially disposed with respect to one another such that they telescope at least partially within one another. When the carrier, pusher, and anchor members 40, 42, 44 are coaxially disposed, the tongues 50, 60, 70 preferably overlap and/or are coextensive with one another, as shown in FIG. 6B). The tabs (only tab 72 is shown in FIG. 6B) may also be aligned with one another. Each of the tongues 50, 60, 70 is preferably tapered to facilitate attachment of the actuator assembly 16, as described further below. The tongues 50, 60, 70 may include holes 51, 61, 71 that may be aligned with one another when the carrier, pusher, and anchor members 40, 50, 60 are aligned within one another. The holes 51, 61, 71 may be sized for receiving a pin 240 (not shown, see FIGS. 3A and 4), or an alignment detent (not shown) for ensuring that the carrier, pusher, and anchor members 40, 50, 60 are properly aligned over one another before using the apparatus 10.

The carrier assembly 14 may be used to deploy a clip 5 or other closure element from the space 15 defined by the carrier assembly 14. In a preferred embodiment, the clip 5 is a generally annular-shaped clip, including one or more barbs and/or tines 7 for engaging the tissue around an opening, e.g., in or adjacent to a wall of a blood vessel (not shown). Preferably, the clip 5 is configured for drawing the tissue around a puncture in the wall of the vessel substantially closed and/or for enhancing hemostasis within the puncture. Exemplary embodiments of a closure element are disclosed in U.S. Pat. No. 6,197,042, in co-pending applications Ser. Nos. 09/546,998 and 09/610,238, and in co-pending application Ser. No. 10/081,726, now U.S. Pat. No. 6,623,510, filed on the same day as the present application, and titled "Closure Apparatus and Methods for Making and Using Them". The disclosures of these references and any others cited therein are expressly incorporated herein by reference.

Returning to FIGS. 1 and 3A, the carrier assembly 14 is actuable from the proximal end 22 of the sheath 12, preferably by the actuator assembly 16. The carrier assembly 14 may be substantially permanently, but slidably, disposed on the sheath 12. For example, the carrier assembly 14 may be initially stored at least partially within the passage 38 under the hub 30, e.g., under the strain relief nose 226. Alternatively, the carrier assembly 14 may be provided separate as a separate assembly (not shown), e.g., with the clip 5 pre-loaded therein, that may be slidably received on the sheath 12.

Turning to FIGS. 1–3B, 7A, and 7B, the actuator assembly 16 generally includes a handle body or housing 74 and a plurality of telescoping actuator members 76, 78, 80. Preferably, the housing 74 includes mating handle covers 74a, 74b, and a nose cover 75 within which the actuator members 76, 78, 80 are slidably mounted. The handle body 74 may include one or more cooperating connectors for connecting the actuator assembly 16 to the sheath 12. For example, the nose cover 75 may include pockets 84 (see FIG. 1) for receiving tabs 34 on the hub assembly 30. Thus, the actuator assembly 16 may be substantially permanently attached to the sheath 12, as described further below. In addition, the actuator assembly 16 may include a frame subassembly 190, and side plates 191, which may secure the obturator assembly 18 relative to the housing 74, as explained further below.

In the preferred embodiment shown in FIGS. 7A and 7B, the telescoping actuator members 76, 78, 80 include an inner tubular member 76, an intermediate tubular member 78, and an outer tubular member 80. Preferably, the actuator members 76–80 are substantially rigid members having longitudinal slots 86, 88, 90 therein, thereby defining generally "C" shaped cross-sections over at least a substantial portion of their lengths. Each of the longitudinal slots 86, 78, 90 may have a width similar to a width of the tongues 50, 60, 70 on the carrier assembly 14, as described further below. The longitudinal slots 86, 78, 90 extend predetermined distances from distal ends 92, 94, 96 of the respective tubular members 76, 78, 80 towards, but not necessarily completely to, their proximal ends (not shown).

The distal ends 92, 94, 96 include detents for engaging respective detents on the carrier assembly 14. For example, the detents may be pockets 104, 106, 108 including a tapered proximal edge and a substantially blunt distal edge (only edges 108a, 108b are shown and labeled in FIG. 7B), similar to the respective tabs 52, 62, 72 on the carrier, pusher, and anchor members 40, 42, 44. Thus, movement of the carrier, pusher, and anchor members 40, 42, 44 may be coupled to the inner, intermediate, and outer actuator members 76, 78, 80, respectively, when the tongues 50, 60, 70 are received in the slots 86, 88, 90.

Returning to FIGS. 1–3A, the actuator assembly 16 also includes a control member, such as knob 110 and shaft 112, that are coupled to the inner, intermediate, and/or outer actuator members 76, 78, 80. Preferably, the shaft 112 is connected only to the intermediate actuator member 78. Thus, axial movement of one or more of the actuator members 76, 78, 80 may be attained by applying an axial force to the knob 110.

The inner, intermediate, and outer actuator members 76–80 include one or more sets of cooperating detents for coupling distal movement of the inner, intermediate, and outer actuator members 76–80 in a predetermined manner, as the knob 110 is directed distally. The term "detents" refers to any combination of mating elements, such as tabs, pockets, slots, ramps, cantilevered members, and the like, that may be selectively or automatically engaged and/or disengaged to couple or decouple the actuator members 76–80 relative to one another. The cooperating detents described below are merely exemplary and not exhaustive.

Preferably, the cooperating detents include a first set of cooperating detents for releasably coupling the outer tubular member 80 to the inner and intermediate tubular members 76, 78. When the carrier assembly 14 reaches a first distal position, e.g., near the distal end 24 of the sheath 12, the outer tubular member 80 may be decoupled and preferably anchored from further substantial axial movement. As the knob 110 is directed further distally, the inner and intermediate tubular members 76, 78, and consequently the carrier and pusher members 40, 42, may continue to be directed distally, while the outer tubular member 80 and the sheath member 44 remain anchored in place.

FIGS. 8A and 8B show a preferred embodiment of a first set of cooperating detents for releasably coupling the outer tubular member 80 to the inner and intermediate tubular members 76, 78. The outer tubular member 80 includes a first detent or tab 114 (or optionally multiple detents, not shown) and the inner and intermediate tubular members 76, 78 include first pockets 116, 118 for receiving the first tab 114 therein. Thus, with the first tab 114 received in the first pockets 116, 118, any axial force (in either direction) moving one of the tubular members 76–80 moves all of them.

First and second ramps 120, 122 are provided on the outer tubular member 80 and the housing 74 of the actuator assembly 16 (only a portion of which is shown) of the sheath 12 (not shown). The first and second ramps 120, 122 slidably engage one another as the actuator members 76, 78, 80 and/or the carrier assembly 14 (not shown) reach the first distal position. Alternatively, the second ramp 122 may be provided on a portion of the hub assembly 30 (not shown). Preferably, the first ramp 120 on the outer tubular member 80 defines a free end of a first cantilevered beam 124 from which the first tab 114 extends inwardly. The beam 124 includes a hole 126 therethrough and the second ramp 122, which is relatively stationary, includes a recess or other feature 128 therein.

The actuator members 76, 78, 80 may be advanced distally (in direction of arrow) until the cooperating first and second ramps 120, 122 slidably engage one another. As the actuator members 76, 78, 80 are advanced further distally, the first ramp 120 slides up onto the second ramp 122, thereby deflecting the first beam 124 outwardly until the first tab 114 is disengaged from the first pockets 116, 118, as shown in FIG. 8B. Further, upon attaining the first distal position, a surface 129 in the hole 126 on the flange 124 and the feature 128 in the second ramp 122 preferably interlock or otherwise contact one another. This contact may secure the outer tubular member 80 from subsequent axial movement, while still allowing the inner and intermediate tubular members 76, 78 to be directed distally beyond the first distal position. In an alternative embodiment, it may be possible to eliminate the ramp 120 on the first beam 124, while still allowing the free end of the first beam 124 to be deflected radially outward by the second ramp 122.

In addition to the first set of cooperating detents described above, the actuator assembly 16 may include a second set of cooperating detents for releasably coupling the inner tubular member 76 and the intermediate tubular member 78 and/or recoupling the inner and outer tubular members 76, 80. Thus, the inner and intermediate tubular members 76, 78 may be directable to a second distal position distal to the first distal position (while the outer tubular member 80 remains substantially stationary). When the carrier and pusher members 40, 42 approach the second distal position, the cooperating detents may decouple the intermediate tubular member 78 from the inner tubular member 76 and/or anchor the inner tubular member 76 in place, e.g., relative to the outer tubular member 80. The intermediate tubular member 78, and consequently the pusher member 42 (not shown), may then be advanced further distally beyond the second distal position, as described further below.

Turning to FIGS. 9A–9D, an exemplary second set of cooperating detents is shown that includes a second tab or other detent 130 on the intermediate tubular member 78 and a second pocket 132 in the inner tubular member 76. The second tab 130 may be received in the second pocket 132 for coupling movement of the inner and intermediate tubular members 76, 78 together.

The outer tubular member 80 includes a spring element 138 that is configured for disengaging the second tab 130 from the second pocket 132 upon attaining the second distal position. For example, the spring element 138 may include a transverse beam 140 that extends from a third cantilevered beam 141 on the outer tubular member 80. The transverse beam 140 extends through slots 142, 144 in the inner and intermediate tubular members 76, 78, e.g., transversely to the longitudinal axis 28, and preferably substantially perpendicular to the longitudinal axis 28.

Preferably, the transverse beam 140 has an inverted "T" shape, as best seen in FIGS. 9C and 9D, defining one or more shoulders 146 adjacent a stem 148. The slots 142, 144 may have narrow regions 142a, 144a and wide regions 142b, 144b proximal to the narrow regions 142a, 144a. Preferably, the narrow regions 142a, 144a have a width less than the shoulders 146, but wider than the stem 148. In contrast, the wide regions 142b, 144b have a width greater than a width of the shoulders 146. In addition, the narrow regions 142a, 144a and wide regions 142b, 144b are disposed along the longitudinal axis 28 at predetermined locations such that the transverse beam 140 coincides with the wide regions 142b, 144b approximately at the second distal position.

Consequently, before the inner and intermediate tubular members 76, 78 reach the second distal position, the shoulders 146 may slide along the outer surface of the intermediate tubular member 78 while the stem 148 slides inside the narrow region 142a, 144a of the slots 142, 144. Alternatively, the shoulders 146 may slide along an outer surface (not shown) of the inner member 76 if the slot 144 is wide its entire length. The tip 150 of the transverse beam 140 may move along the inner tubular member 76, e.g., at a predetermined clearance from the inner surface thereof such that the tip 150 does not touch the inner surface of the inner tubular member 76. Alternatively, the tip 150 may slide along the inner surface of the inner tubular member 76.

When the inner and intermediate tubular members 76, 78 approach or attain the second distal position, the shoulders 146 may enter the wide regions 142b, 144b, e.g., due to the bias of the beam 141. This action may produce two substantially simultaneous results. First, when the shoulders 146 enter the wide regions 142b, 144b, i.e., such that the beam 140 moves transversely, the tip 150 of the beam 140 may push the second tab 130 radially outward, thereby disengaging the second tab 130 from the second pocket 132. Thus, further distal movement of the intermediate tubular member 78 may be allowed independent of the inner tubular member 76. In addition, the shoulders 146 of the beam 140 may enter the wide region 142b of the slot 142. Because the wide region 142b has a size corresponding substantially to a cross-section of the transverse beam 140, the inner tubular member 76 is consequently coupled to the outer tubular member 80 as it is disengaged from the intermediate tubular member 78.

Thus, the inner tubular member 76 may be substantially locked in place, e.g., to the outer tubular member 80 since the outer tubular member 80 has been previously secured in place. Preferably, these two actions, i.e., releasing the intermediate tubular member 80 and securing the inner tubular member 76 in place occur substantially simultaneously.

Returning to FIGS. 1–3B, the actuator assembly 16 also includes the obturator assembly 18 mounted within the housing 74. Generally, the obturator assembly 18 includes a flexible or semi-rigid tubular body or other elongate rail 172 having a proximal end 174, a distal end 176, and a distal portion 184. An actuator rod, wire, or other elongate member 178 is slidably disposed with respect to the rail 172, e.g., within a lumen of the rail 172.

In addition, the obturator assembly 18 includes an obturator housing 180 on the proximal end 174 of the rail 172. The obturator housing 180 may include one or more tabs 192 for engaging complementary slots 194 in the side plates 191. Thus, the obturator assembly 18 may be secured within the housing 74 of the actuator assembly 16 when the tabs 192 are received in the slots 194. The side plates 191 may be connected to the frame subassembly 190, and the handle covers 74a, 74b are secured over the side plates 191. When the obturator assembly 18 is mounted within the housing 74, the rail 172 may extend through the actuator members 76, 78, 80, e.g., until the distal portion 182 extends beyond the distal ends 92, 94, 96 of the actuator members 76, 78, 80.

Figure 10B:
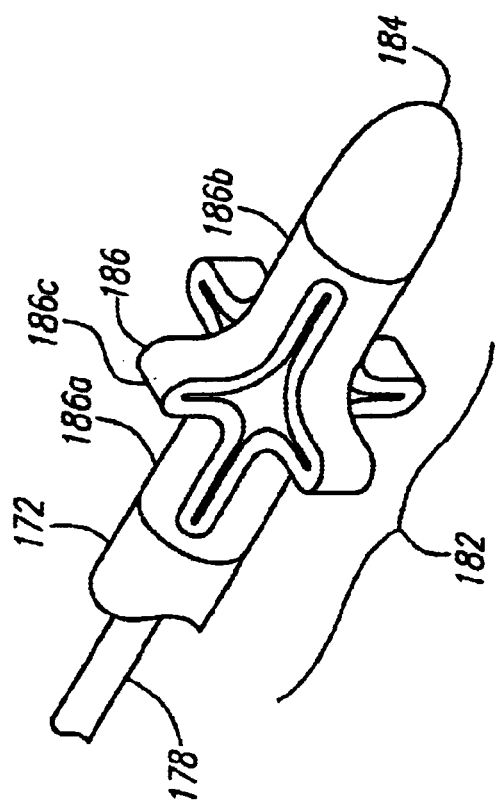
FIGS. 10A and 10B are perspective views of the distal end of the obturator of FIG. 3B, showing positioning elements on the obturator in collapsed and expanded configurations, respectively.
Figure 10A:
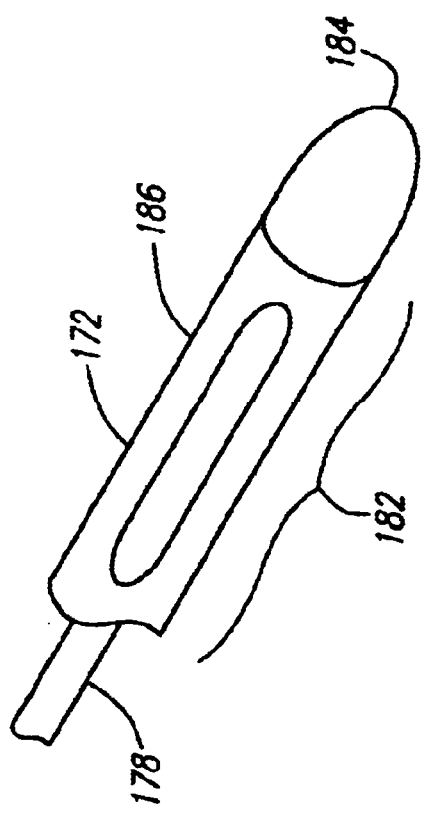

Turning to FIGS. 10A and 10B, the distal portion 182 of the obturator assembly 18 includes a substantially rounded, soft, and/or flexible distal tip 184. Optionally, the distal tip 184 may include a pigtail (not shown) that may facilitate atraumatic advancement of the distal portion 182 into a blood vessel or other body lumen (not shown). The obturator assembly 18 preferably has a length relative to the sheath 12 such that the distal portion 182 extends beyond the distal end 24 of the sheath 12 when the obturator assembly 18 is in a deployed position (shown in FIGS. 12C and 12D), as explained below.

One or more, and preferably a plurality of, positioning elements 186 are provided on the distal portion 182 that may be selectively expandable between a substantially axial collapsed configuration (shown in FIG. 10A) and a substantially transverse expanded configuration (shown in FIG. 10B). Preferably, the positioning elements 186 are substantially flexible splines configured for expanding substantially transversely with respect to the longitudinal axis 28.

In one embodiment, the obturator assembly 18 includes four splines 186 that are substantially equally spaced about the distal portion 182. Alternatively, the obturator assembly 18 may include a pair of splines (not shown) that are disposed generally opposite one another about the distal portion. The obturator assembly 18 may include more or fewer splines without deviating from the scope of the present invention. Additional embodiments of positioning elements are disclosed in co-pending application Ser. No. 09/732,835, the disclosure of which is expressly incorporated herein by reference.

Optionally, the splines 186 may include radiopaque markers (not shown) or may be wholly or partially formed from radiopaque material to facilitate observation of the splines 186 using fluoroscopy or other imaging systems. Alternatively, or in addition, the carrier assembly 14 may include one or more radiopaque markers, e.g., at its distal end (not shown) and/or the clip 5 may include radiopaque marker(s) or may be made from radiopaque material. This may facilitate monitoring the location of the clip 5 relative to the splines 186, as described further below.

Returning to FIGS. 10A and 10B, each spline 186 preferably has a first fixed (e.g., proximal) end 186a and a second movable (e.g., distal) end 186b. The second end 186b may be axially movable towards the first end 186a to cause an intermediate region 186c of the spline 186 to buckle and/or expand transversely outwardly, thereby defining the substantially transverse expanded configuration. In a preferred embodiment, an actuator rod 178 extends through the distal portion 182 and is coupled to the distal tip 184 of the obturator assembly 18 and/or to one of the first and second ends 186a, 186b. The actuator rod 178 may be moved axially, e.g., proximally, with respect to the rail 172 to selectively expand the splines 186 between their collapsed configuration and their expanded configuration.

Figure 12A:
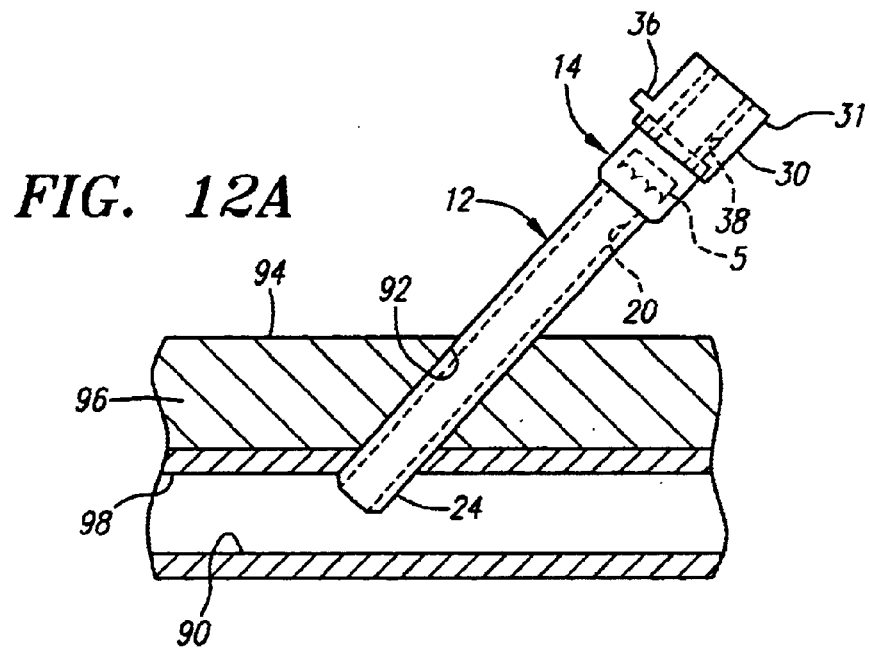
FIGS. 12A–12H are cross-sectional views of a blood vessel, showing a method for delivering a clip into an interstitial region of a passage communicating with the vessel.
Figure 12B:
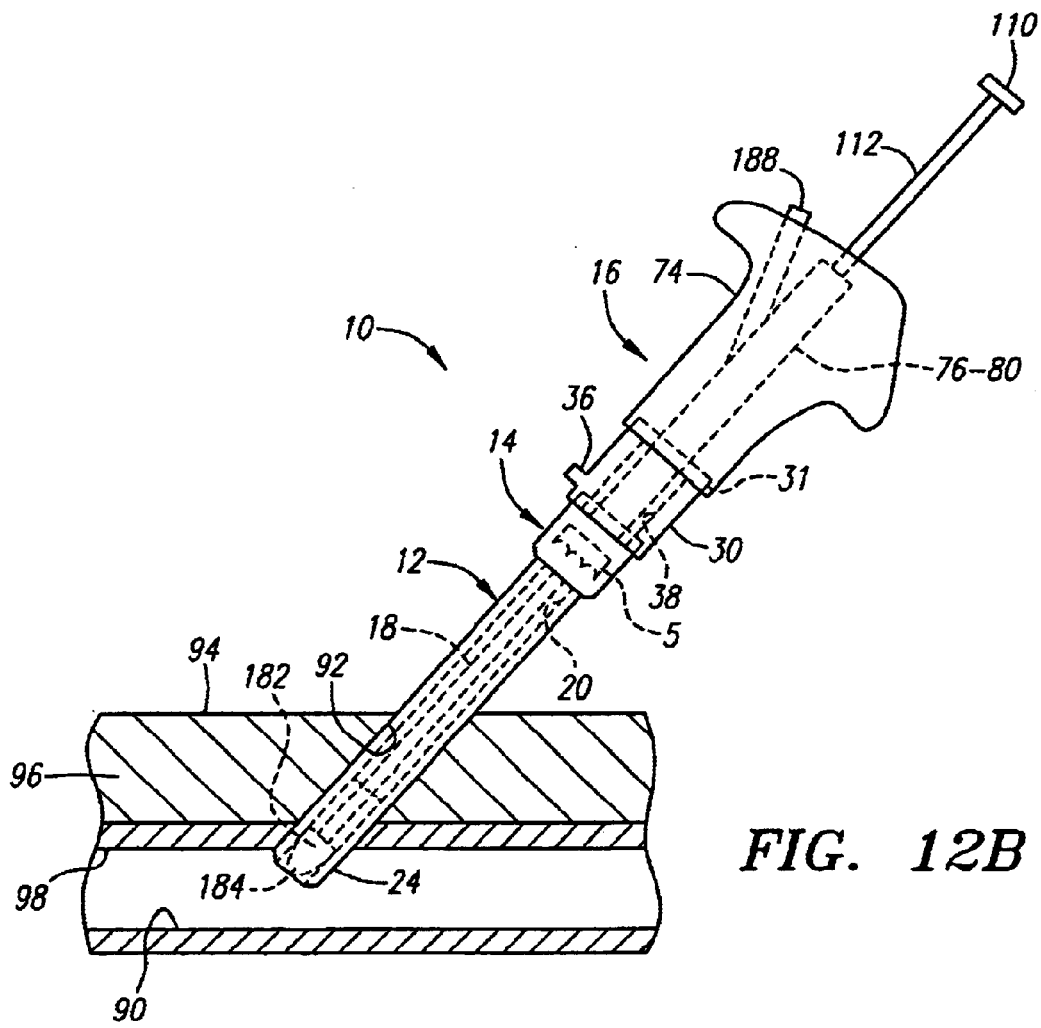
Figure 12C:
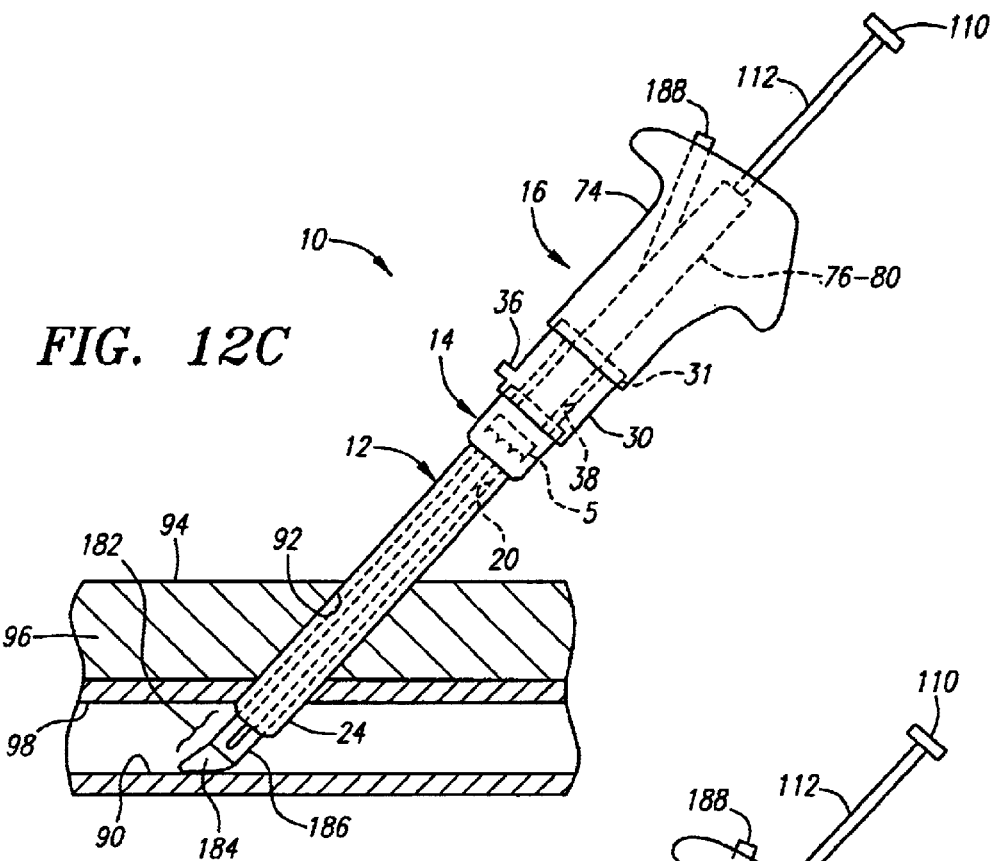
Figure 12D:
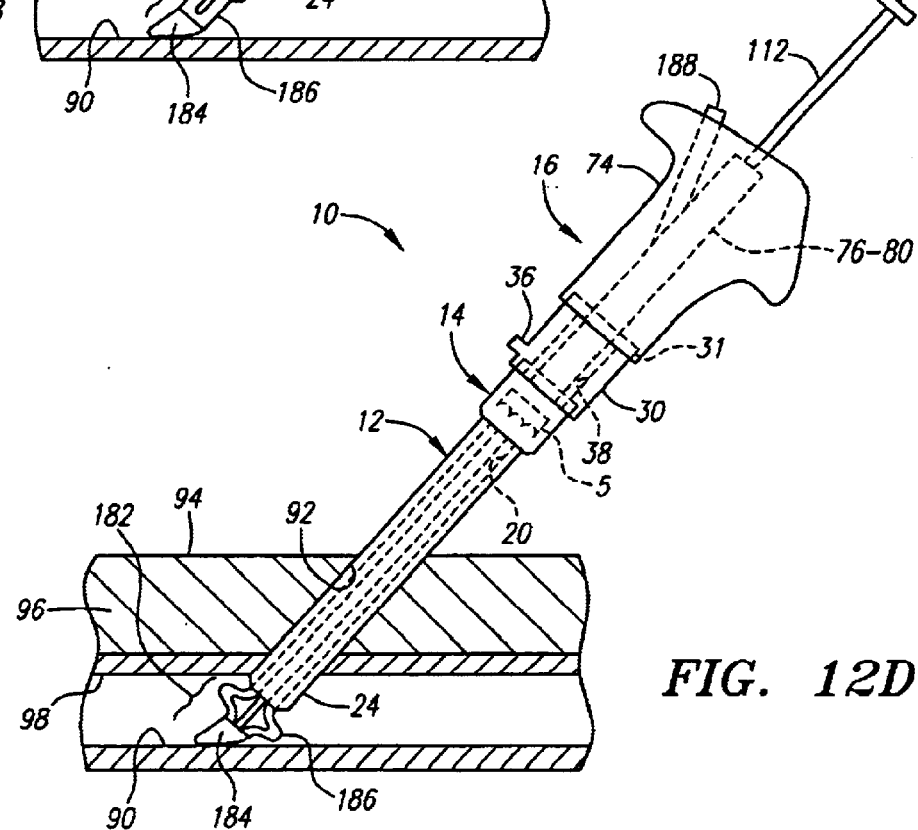

Turning to FIGS. 12B–12D, the obturator housing 180 (not shown, see FIG. 3A) is configured for selectively deploying the distal portion 182 and/or moving the splines 186 between their collapsed and expanded configurations. For example, the obturator housing 180 may include a switch 188 that may be depressed or rotated. Initially, as shown in FIG. 12B, the distal portion 182 may be retracted within the distal end 24 of the sheath 12. As the switch 188 is activated, e.g., depressed, the distal portion 182 may be deployed from the distal end 24 of the sheath 12, as shown in FIG. 12C. As the switch is further depressed, the splines 186 may be expanded to the expanded configuration, as shown in FIG. 12D.

For example, the rail 172 and rod 178 may initially be moved together, e.g., to deploy the distal portion 182, as shown in FIG. 12C. Once deployed, the rod 178 may stop moving, the rail 172 may continue to advance, thereby buckling the splines 186 as the first and second ends 186a, 186b become closer to one another, as shown in FIG. 12D. Alternatively, after deploying the distal portion 182, the rod 178 may be retracted proximally to expand the splines 186.

The obturator housing 180 (see FIG. 3A) preferably includes a lock 189 for securing the rod 178 and rail 172 relative to one another, e.g., to lock the splines 186 in their expanded configuration. The lock may be released, for example, by depressing the switch 188 again, by activating an emergency release (not shown) and/or by activating a release mechanism (not shown) when the carrier assembly 14 is advanced, as explained below. The obturator housing 180 may include a spring or other biasing mechanism (not shown) for biasing the rail 172 and/or rod 178 to return the splines 186 to their collapsed configuration and/or to retract the distal portion 182 back into the sheath 12 when the lock is released. For example, the lock may be released upon advancing the actuator members 76, 78, 80 to a predetermined position, e.g., before or after attaining the second distal position, as explained further below.

Alternatively, as shown in FIGS. 11A and 11B, an apparatus 310 for delivering a closure element 5 may be provided that includes a separate obturator assembly 318 that may be inserted into or otherwise connected to an actuator assembly 316. For example, the actuator assembly 316 may include a lateral port 352 with an inner passage 354 that communicates with an interior region or lumen (not shown) of actuator members 376–380 of the actuator assembly 316.

At any time before advancing the carrier assembly 314 to deploy the clip 5 thereon, the obturator assembly 318 may be inserted into the lateral port 352, thereby introducing a distal portion 382 of the obturator assembly 318 into the sheath 312. An obturator housing 381 of the obturator assembly 318 may include one or more detents (not shown) for engaging complementary-shaped detents (also not shown) on the lateral port 352. Thus, the obturator assembly 318 may be substantially secured axially with respect to the lateral port 352, and consequently relative to the actuator assembly 316 and sheath 312. Otherwise, the actuator and obturator assemblies 316, 318 may operate similar to the previous embodiment.

Turning to FIGS. 12A–12H, an apparatus 10 (the entire apparatus 10 is shown in FIGS. 12B–12F), such as that shown in FIG. 1, may be used to deliver a closure device, such as a clip 5, to close and/or seal an incision, puncture, or other opening. For example, the apparatus 10 may be used to deliver the clip 5 through a passage 92 that extends from a patient's skin 94, through intervening tissue 96, and into a wall 98 of a blood vessel 90. Alternatively, the apparatus 10 may be used to deliver other annular shaped devices (not shown) that may be disposed within the carrier assembly 14.

As shown in FIG. 12A, the sheath 12, without the actuator assembly 16 (not shown), may be inserted or otherwise positioned within the blood vessel 90, i.e., through the passage 92. The sheath 12 is preferably provided with the carrier assembly 14 in its proximal position, e.g., adjacent to or within the hub assembly 30. The sheath 12 may be advanced over a guide wire or other rail (not shown) previously positioned through the passage 92 into the blood vessel 90 using conventional procedures. Preferably, the blood vessel 90 is a peripheral vessel, such as a femoral or carotid artery, although other body lumens may be accessed using the sheath 12, as will be appreciated by those skilled in the art.

The passage 92, and consequently the sheath 12, may be oriented with respect to the vessel 90, thereby facilitating introduction of devices through the lumen 20 of the sheath 12 into the vessel 90 with minimal risk of damage to the vessel 90. One or more devices, such as a guide wire, a catheter, and the like (not shown), may be inserted through the sheath 12 and advanced to a desired location within the patient's body. For example, the devices may be used to perform a therapeutic or diagnostic procedure, such as angioplasty, atherectomy, stent implantation, and the like, within the patient's vasculature. After the procedure is complete, the device(s) may be removed from the sheath 12, and the actuator assembly 16 may be attached to the hub assembly 30 of the sheath 12.

Turning to FIGS. 12B, along with FIGS. 7A, and 7B, the longitudinal slots 86–90 in the actuator members 76, 78, 80 may be aligned with the side port 36 extending from the hub assembly 30. This may align the "C" shaped cross-sections of the tubular members 76–80 with the spoke (not shown) extending across the passage 38. The distal portion 182 of the obturator assembly 18 may then be inserted into the lumen 20 of the sheath 12, and advanced towards the distal end 24 of the sheath 12. The actuator members 76, 78, 80 may also be inserted into the passage 38, thereby disposing the distal portion 182 in a predetermined rotational orientation relative to the sheath 12. Once the actuator members 76, 78, 80 are fully received in the passage 38, the connectors 34, 84 (not shown, see FIG. 1) may engage to secure the actuator assembly 16 to the hub assembly 30.

The carrier assembly 14 is also disposed at least partially within the passage 38 (not shown in FIGS. 7A and 7B) such that the tongues 50, 60, 70 on the carrier, pusher, and anchor members 40, 42, 44 are aligned with the side port 36. Consequently, the tongues 50, 60, 70 may be aligned with the longitudinal slots 86, 88, 90 in the actuator members 76, 78, 80 as the actuator members 76, 78, 80 are inserted into the passage 38.

Thus, as the actuator members 76, 78, 80 are advanced into the passage 38, the tongues 50, 60, 70 may be received in the longitudinal slots 86, 88, 90, preferably until the tabs 52, 62, 72 are received in the pockets 104, 106, 108, as best seen in FIG. 7B. The tongues 50, 60, 70 are preferably at least partially tapered, thereby self-aligning with the longitudinal slots 86, 88, 90, e.g., to correct any slight misalignment. With the tongues 50, 60, 70 engaged within the longitudinal slots 86, 88, 90, the carrier, pusher, and sheath members 40, 42, 44 may be coupled to the inner, intermediate, and outer tubular members 76, 78, 80, respectively. Thus, once the actuator assembly 16 is secured to the hub assembly 30, the distal portion 182 of the obturator assembly 16 is preferably disposed adjacent the distal end 24 of the sheath 12 within the lumen 20, as best seen in FIG. 12B.

Alternatively, for the apparatus 310 shown in FIGS. 11A and 11B, the actuator assembly 316 may be attached to the hub assembly 330 without the obturator assembly 318. The obturator assembly 318 may then be inserted into the lateral port 352, through the interior of the actuator members 376–380, and into the lumen 320 of the sheath 312 at any time before deploying the clip 5. Thus, the distal portion 382 of the obturator assembly 318 may be disposed adjacent the distal end 324 of the sheath 312, similar to the actuator assembly 16.

Turning to FIG. 12C, the distal portion 182 of the obturator 18 may be advanced beyond the distal end 24 of the sheath 12, for example, by depressing the switch 188 on the actuator assembly 16. The distal tip 184 preferably is substantially soft and/or flexible such that the distal portion 182 substantially atraumatically enters the vessel 90. In this fully inserted position, cooperating detents (not shown), e.g., on the actuator housing 180 and the rail 172 of the actuator assembly 16, may be engaged to substantially secure the distal end 182 of the obturator 18 beyond the distal end 24 of the sheath 12.

Turning to FIG. 12D, the splines 186 may then be directed to their expanded configuration, for example, by further depressing the switch 188 on the actuator assembly 16. Preferably, the distal portion 182 is deployed and the splines are expanded in a single motion, e.g., by activating the switch 188. Alternatively, these steps may be performed independently from one another if desired.

Figure 12E:
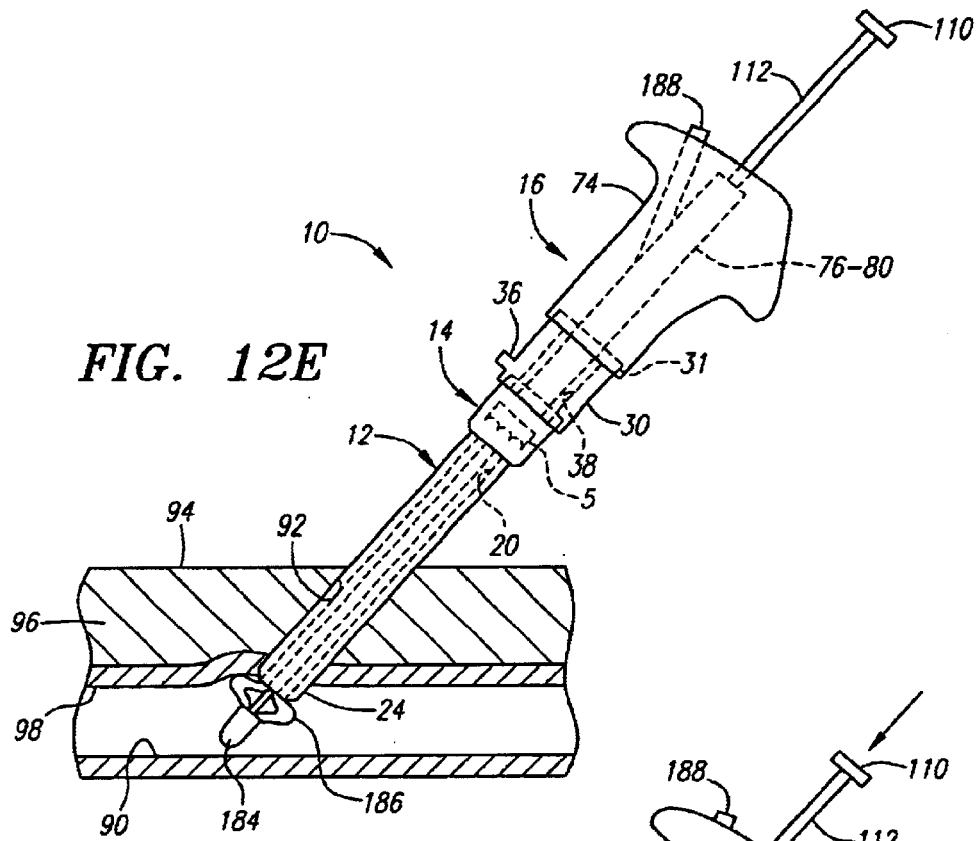

Turning to FIG. 12E, the entire apparatus 10, including the sheath 12 and splines 186, may then be moved, e.g., by manipulating the actuator assembly 16. Preferably, the apparatus 10 is partially withdrawn from the vessel 90 until the splines 186 contact the wall 98 of the vessel 90, as shown. Thus, the splines 186 may provide a tactile indication of the position of the distal end 24 of the sheath 12 with respect to the wall 98 of the vessel 90. In addition, the splines 186 may assist in "presenting" the wall 98 of the vessel 90, e.g., for receiving the clip 5 (or other closure element) if the clip 5 is to engage the wall 98.

Figure 12F:
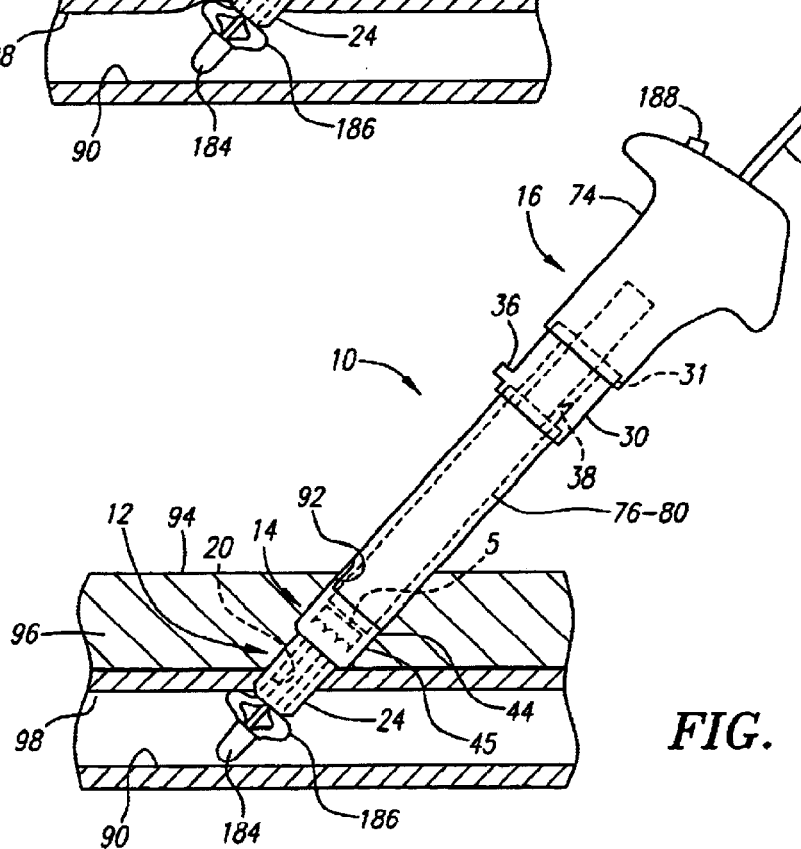

Turning to FIG. 12F, with the sheath 12 properly positioned, the carrier assembly 14 may be advanced along the sheath 12, i.e., into the passage 92 to deliver the clip 5. For example, a distal force may be applied to the knob 110, thereby advancing the actuator members 76, 78, 80 and consequently the carrier assembly 14 distally over the sheath 12. Because the actuator members 76, 78, 80 are all coupled together, as described above, the carrier assembly 14 advances with the outer sleeve 45 on the anchor member 44 substantially covering the clip 5. Because of the tapered configuration of the outer sleeve 45 and the carrier member 40, the carrier assembly 14 may be advanced through the passage 92 substantially atraumatically. In addition, because the clip 5 is substantially covered by the outer sleeve 45, the tissue surrounding the passage 92 may not be exposed to the tines 7 on the clip 5, which otherwise may inadvertently catch the tissue and damage the tissue and/or the clip 5. Further, the outer sleeve 45 may facilitate advancing the carrier assembly 14 through intervening layers of tissue, such as one or more layers of fascia (not shown) that may be encountered between the skin 94 and the wall 98 of the vessel 90.

When the carrier assembly 14 reaches a first distal position (FIG. 12F), the first set of cooperating detents (not shown, but described above with reference to FIGS. 8A and 8B) are disengaged to release the outer tubular member 80 with respect to the inner and intermediate tubular members 76, 78. The first beam 124 on the outer tubular member 80 may slidably engage the second ramp 122 on the housing 74, thereby disengaging the first tab 114 from the first pockets 116, 118. In addition, the outer tubular member 80 is preferably substantially secured at the first distal position, e.g., when the hole 126 in the first beam 124 interlocks a recess 128 in the second ramp 122 (as shown in FIG. 8B).

Figure 12G:
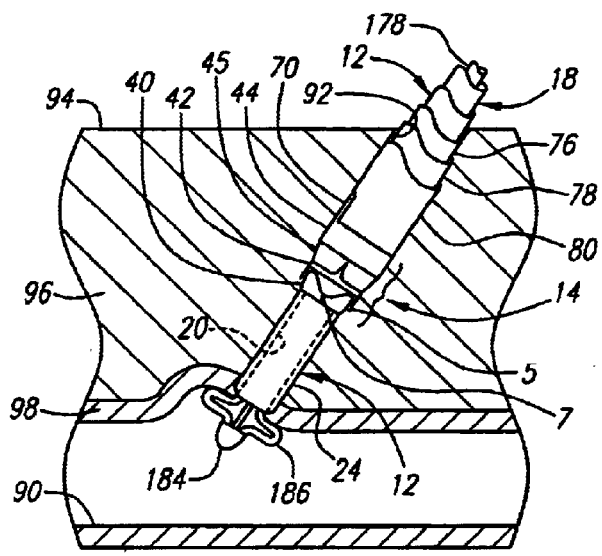

Turning to FIG. 12G, as the distal force continues to be applied to the knob 110 (not shown), the inner and intermediate tubular members 76, 80, and consequently the carrier and pusher members 40, 42, may be advanced further distally. As the carrier and pusher members 40, 42 are advanced relative to the outer sleeve 45, they may cause the outer sleeve 45 to expand to accommodate their advancing between the outer sleeve 45 and the sheath 12. To facilitate this advancement without tearing the outer sleeve 45, the outer sleeve 45 may include longitudinal slots, e.g., either straight slots 45a, as shown in FIG. 6C, or spiral slots 45a,' as shown in FIG. 6D. The slots 45a, 45a' may open as the carrier and pusher members 40, 42 are advanced, such that the outer sleeve 45 expands to assume a zigzag mesh configuration. In particular, the spiral slots 45a' may translate axial forces to torsional forces due to the spiral shape of the slots 45a,' e.g., such that the outer sleeve 45' twists as it expands, causing the surrounding tissue 96 to rotate about the longitudinal axis 28, thereby minimizing the tissue 96 being pushed distally as the carrier and pusher members 40, 42 are advanced through the tissue 96.

When the carrier and pusher members 40, 42 reach a second distal position, the second set of cooperating detents (not shown, but described above with reference to FIGS. 9A–9D) interact to release the intermediate tubular member 78 from the inner tubular member 76. For example, the transverse beam 140 may push the second tab 130 out of the second pocket 132 (as best seen in FIG. 9B). In addition, substantially simultaneously with this action, the second set of detents also preferably substantially secure the inner tubular member 76, e.g., by interlocking the transverse beam 140 in the wide portion 142b of slot 142.

Figure 12H:
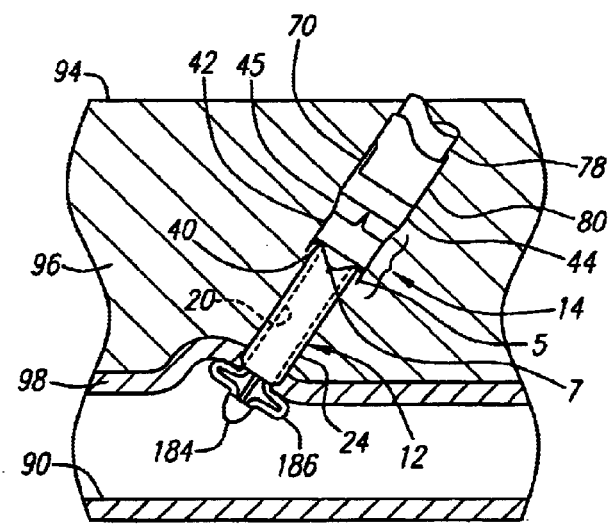

As shown in FIG. 12H, the intermediate tubular member 78 may then be advanced further distally by continuing to apply a distal force to the knob 110 (not shown). Thus, the pusher member 42 may be advanced distally relative to the carrier member 40, thereby forcing the clip 5 distally off the carrier member 40 and preferably into engagement with the wall 98 of the vessel 90 or other tissue surrounding the passage 92.

Figure 12I:
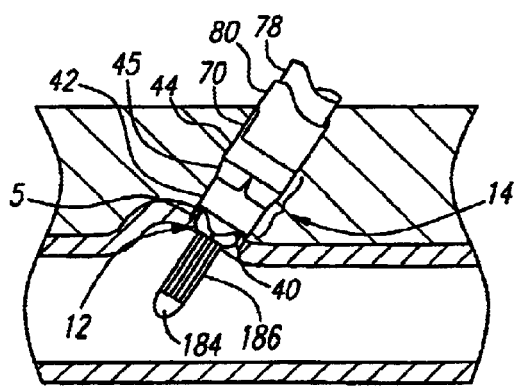
FIG. 12I is a cross-sectional view of the vessel of FIGS. 12A–12H, showing an alternative method wherein the clip is delivered into the wall of the vessel.

In a preferred method, shown in FIG. 12I, the splines 186 may automatically return to their collapsed configuration and/or may be retracted into the sheath 12 during deployment of the clip 5. For example, the splines 186 may be collapsed as the clip 5 is partially deployed from the carrier assembly 14, e.g., before the clip 5 is completely collapsed towards its closed position. The orientation of the clip 5 and the splines 186 about the longitudinal axis 28 may be such that tines 7 of the clip 5 are disposed between the splines 186 as the clip 5 is deployed. Thus, as the tines 7 are driven into the wall of the vessel 90, the tines 7 may avoid being driven into the splines 186. Embodiments of a clip and delivery apparatus that provide such an orientation are disclosed in application Ser. No. 09/478,179, incorporated by reference above.

For example, as the intermediate tubular member 78 is advanced to a third position beyond the second distal position, it may release the lock in the obturator housing 180, thereby causing the splines 186 to collapse and/or the distal portion 182 to retract into the sheath 12. Alternatively, the splines 186 may be collapsed before the clip 5 is ejected completely from off of the carrier member 40, or even before the pusher member 42 begins to deploy the clip 5. This may avoid any risk of contact between the clip 5 and the splines 186.

The relative lengths of the actuator members 76, 78, 80 and the sheath 12 and/or the length of the longitudinal slots 86, 88, 90 may be set such that the second distal position is at a region proximal to the wall 98 of the vessel 90. For example, as shown in FIG. 12H, it may be desirable to deploy the clip 5 within intervening tissue between the patient's skin and the wall 98 of the vessel 90. Alternatively, as shown in FIG. 12I, the clip 5 may be deployed such that the tines 7 are driven into or through the wall 98 of the vessel 90.

Once the clip 5 is successfully delivered, the apparatus 10 may be withdrawn from the passage 92. If the splines 64 of the locator member 14 are not automatically collapsed during advancement of the housing 24, the splines 64 may be affirmatively collapsed, e.g., by depressing the switch 188. The entire apparatus 10 may then be removed in one step. Alternatively, as in the embodiment of FIGS. 11A and 11B, if the obturator assembly 318 is separable from the actuator assembly 316, it may be withdrawn from the sheath 12 before withdrawing the actuator assembly 316 and/or sheath 312.

Thus, the clip 5 remains in place within the wall 98 of the vessel 90 or in the surrounding tissue 96 adjacent the vessel 90 to close and/or seal the passage 92. The clip 5 may remain substantially permanently in the patient's body. Alternatively, the clip 5 may be formed from bioabsorbable material, and may remain until the passage 92 is at least partially healed and the clip 5 is absorbed by the surrounding tissue 96.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for delivering a closure element into an opening through tissue, comprising:
    an elongate member comprising proximal and distal ends;
    a carrier assembly slidable on the elongate member, the carrier assembly comprising an inner carrier member, a middle pusher member, and an outer sleeve member, each member comprising an annular body including a connector on its proximal end, the pusher member disposed about the carrier member, thereby defining a space distal to the pusher member along an outer surface of the carrier member, the outer sleeve member extending at least partially over the space; and
    an annular-shaped element received on the carrier member within the space, the annular-shaped element being deployable from the space upon distal movement of the pusher member relative to the carrier member.

2. The apparatus of claim 1, further comprising an actuator assembly comprising an actuator housing and inner, intermediate, and outer actuator members that telescope relative to the actuator housing, the actuator housing extending from the proximal end of the elongate member, each actuator member comprising a connector on its distal end for engaging a respective connector on the carrier assembly, thereby coupling movement of the carrier, pusher, and outer sleeve members to the inner, intermediate, and outer actuator members, respectively.

3. The apparatus of claim 2, wherein the actuator assembly comprises a control member, and the inner, intermediate, and outer actuator members comprise a first set of cooperating detents for coupling distal movement of the inner, intermediate, and outer actuator members as the control member is directed distally, the first set of cooperating detents releasing the outer actuator member upon attaining a first distal position, thereby permitting further distal movement of the inner and intermediate actuator members, and consequently permitting the carrier and pusher members to be directed distally beyond the outer sleeve member.

4. The apparatus of claim 3, wherein the control member is coupled to one of the inner actuator member and the intermediate actuator member, and wherein the first set of cooperating detents comprise a first detent on the outer actuator member and first pockets in the inner and intermediate actuator members for receiving the first detent therein, the apparatus further comprising cooperating ramps on at least one of the actuator housing and the outer actuator member, the cooperating ramps being configured for disengaging the first detent from the first pockets upon attaining the first distal position, thereby allowing the inner and intermediate actuator members to be directed distally beyond the first distal position.

5. The apparatus of claim 3, further comprising a second set of cooperating detents on the intermediate actuator member and the inner actuator member for coupling movement of the inner and intermediate actuator members together.

6. The apparatus of claim 5, wherein the second set of cooperating detents comprises a second detent on the intermediate actuator member and a second pocket on the inner actuator member.

7. The apparatus of claim 6, wherein the inner and intermediate actuator members are directable to a second distal position distal to the first distal position, and wherein one of the actuator housing and the outer actuator member comprises a spring element for disengaging the second detent from the second pocket upon attaining the second distal position.

8. The apparatus of claim 7, wherein the control member is coupled to the intermediate actuator member, and wherein the intermediate actuator member may be advanced distally beyond the second distal position by directing the control member further distally, thereby directing the pusher member distally with respect to the carrier member to deploy the annular-shaped element from the space.

9. The apparatus of claim 7, wherein the spring element comprises a beam extending from the outer actuator member through slots in the inner and intermediate actuator members, the beam being received in the second pocket upon attaining the second distal position, thereby disengaging the second detent and allowing further distal movement of the intermediate member while substantially simultaneously coupling the inner and outer actuator members together.

10. The apparatus of claim 2, further comprising:
    a locator member connected to the actuator assembly, the locator member having a distal portion extendable distally beyond the distal end of the elongate member;
    one or more positioning elements on the distal portion of the locator member, the positioning elements being expandable from a collapsed configuration towards a transversely expanded configuration; and
    a locking mechanism on the locator member for releasably retaining the positioning elements in the expanded configuration.

11. The apparatus of claim 10, wherein the elongate member comprises an introducer sheath, and the locator member comprises an obturator insertable into a lumen of the sheath.

12. The apparatus of claim 11, wherein the obturator is insertable into the actuator housing and into the lumen of the sheath until the positioning elements are disposed beyond the distal end of the sheath.

13. The apparatus of claim 12, wherein the obturator and actuator housing including cooperating detents for substantially securing the obturator to the actuator housing.

14. The apparatus of claim 12, wherein at least one of the inner, intermediate, and outer actuator members comprises a third detent for engaging a release mechanism within the actuator housing for disengaging the locking mechanism on the locator member, thereby collapsing the positioning elements to the collapsed configuration upon advancement of the at least one of the inner, intermediate, and outer actuator members to a predetermined distal position.

15. The apparatus of claim 2, wherein the inner, intermediate, and outer actuator members comprise tubular members including "C" shaped cross-sections over at least substantial portions of their lengths.

16. The apparatus of claim 2, further comprising a hub on the proximal end of the elongate member, the hub and the housing comprising cooperating connectors for securing the actuator assembly to the elongate member.

17. The apparatus of claim 16, wherein the hub and the elongate member define a passage therebetween, and wherein the carrier assembly is at least partially disposed within the passage.

18. The apparatus of claim 1, wherein the annular-shaped element comprises a closure element including a plurality of tissue engaging elements oriented distally along the outer surface of the carrier member.

19. The apparatus of claim 1, wherein the outer sleeve member extends distally over the carrier member such that a distal end of the outer sleeve member slidably surrounds an outer surface of the elongate member.

20. The apparatus of claim 19, wherein at least one of the carrier member and the pusher member is slidable distally relative to the outer sleeve member, the outer sleeve member being expandable to accommodate at least one of the carrier member and the pusher member sliding between the outer sleeve member and the outer surface of the elongate member.

21. The apparatus of claim 20, wherein the outer sleeve member comprises a plurality of longitudinal slots therein, the slots opening as at least one of the carrier member and the pusher member is slid distally to expand the outer sleeve member.

22. The apparatus of claim 21, wherein the plurality of longitudinal slots are staggered such that the outer sleeve member assumes a zigzag mesh configuration as it expands.

23. The apparatus of claim 21, wherein the plurality of longitudinal slots have a spiral shape.

24. The apparatus of claim 19, wherein the outer sleeve member extends at last about fifteen millimeters beyond a distal end of the carrier member before at least one of the carrier member and the pusher member is advanced relative to the outer sleeve member.

25. An apparatus for delivering a closure device from a carrier assembly slidably carried by an elongate member, comprising:
 a housing comprising proximal and distal ends, the distal end comprising a connector for mating to a proximal end of the elongate member;
 inner, intermediate, and outer actuator members that are nested together and telescope relative to the housing, each actuator member comprising a connector on its distal end for engaging a respective member on the carrier assembly, thereby coupling distal movement of the carrier assembly to distal movement of the inner, intermediate, and outer actuator members;
 a control member coupled to at least one of the inner, intermediate, and outer actuator members;
 cooperating detents on the inner, intermediate, and outer actuator members for coupling together distal movement of the inner, intermediate, and outer actuator members as the control member is directed distally, the cooperating detents releasing the outer actuator member upon attaining a first distal position, thereby permitting further distal movement of the inner and intermediate actuator members with respect to the outer actuator member.

26. The apparatus of claim 25, wherein the control member is coupled to one of the inner actuator member and the intermediate actuator member, and wherein the cooperating detents comprise first cooperating detents on the inner, intermediate, and outer actuator members, the apparatus further comprising cooperating ramps on at least one of the housing and the outer actuator member, the cooperating ramps being configured for disengaging the first cooperating detents upon attaining the first distal position, thereby allowing the inner and intermediate actuator members to be directed distally beyond the first distal position by the control member.

27. The apparatus of claim 26, wherein the cooperating detents further comprise second cooperating detents on the inner and intermediate actuator members for coupling distal movement of the inner and intermediate tubular members together, and wherein one of the housing and the outer actuator member comprises an element for disengaging the second cooperating detents upon attaining a second distal position distal to the first distal position.

28. The apparatus of claim 27, wherein the control member is coupled to the intermediate actuator member, and wherein the intermediate actuator member may be advanced distally beyond the second distal position by directing the control member further distally, thereby directing the pusher member distally with respect to the carrier member to deploy the closure element from an annular space.

29. An apparatus for delivering a closure device, comprising:
 a sheath comprising a lumen extending between proximal and distal ends, and including a carrier assembly slidably carried by the sheath, the carrier assembly comprising a closure element carried by the carrier assembly;
 an actuator assembly comprising an actuator housing connected to the proximal end of the sheath, a plurality of telescoping actuator members connected to the carrier assembly;
 an obturator in the actuator housing, a distal portion of the obturator extending through the lumen of the sheath and beyond a distal end of the sheath, the distal portion comprising one or more positioning elements expandable from a collapsed configuration to a transverse expanded configuration, the obturator also comprising a locking mechanism for releasably securing the positioning elements in the expanded configuration; and
 a release mechanism in the actuator housing coupled to at least one of the telescoping actuator members and the obturator, the release mechanism automatically releasing the locking mechanism when the at least one of the telescoping actuator members is advanced distally to a predetermined location to contract the positioning elements to the collapsed configuration.

30. An apparatus for delivering a closure element into an opening through tissue, comprising:

an elongate member comprising proximal and distal ends;

a carrier assembly slidable on the elongate member, the carrier assembly comprising an inner carrier member, and a pusher member overlying the carrier member, thereby defining a space distal to the pusher member along an outer surface of the carrier member;

an annular-shaped closure element received on the carrier member within the space, the closure element being deployable from the space upon distal movement of the pusher member relative to the carrier member; and an actuator assembly connected to the proximal end of the elongate member, the actuator assembly comprising a plurality of telescoping members coupled to the carrier assembly, the actuator assembly configured for advancing the carrier assembly distally to a predetermined position, whereupon the pusher member is movable distally with respect to the inner carrier member for deploying the closure element from the space.

31. The apparatus of claim 30, wherein the carrier assembly further comprises an outer sleeve member extending at least partially over the space, thereby at least partially covering the closure element, the actuator assembly configured for limiting distal movement of the outer sleeve member such that the closure element is at least partially exposed from the outer sleeve member before the carrier assembly attains the predetermined position.

32. A method for delivering a closure element to close an opening through tissue, the method comprising:

inserting a distal end of an elongate member into an opening through tissue;

advancing a carrier assembly over the elongate member towards the distal end of the elongate member, the carrier assembly comprising a carrier member carrying a closure element, and an outer sleeve covering the closure element;

discontinuing advancing the outer sleeve, while continuing to advance the carrier member and the closure element, thereby causing the outer sleeve to expand as the carrier member and the closure element pass thereunder; and deploying the closure element from the elongate member to close the opening.

33. The method of claim 32, wherein the deploying step comprises withdrawing the elongate member from the opening.

34. The method of claim 32, wherein the carrier assembly further comprises a pusher member, and wherein the deploying step comprises advancing the pusher member relative to the carrier member, thereby deploying the closure element from the carrier assembly.

35. The method of claim 32, wherein the outer sleeve comprises a weakened region extending towards the distal end of the elongate member, the weakened region tearing as the carrier member and closure element are advanced relative to the outer sleeve.

36. The method of claim 32, wherein the outer sleeve comprises a plurality of longitudinal slots, the slots opening as the carrier member and closure element are advanced relative to the outer sleeve, thereby expanding the outer sleeve.

37. The method of claim 36, wherein the longitudinal slots are staggered relative to one another such that the outer sleeve assumes a zigzag mesh configuration as it expands.

38. The method of claim 36, wherein the slots comprise spiral slots, the outer sleeve twisting as it expands.

39. The method of claim 32, wherein the opening through tissue extends through one or more layers of fascia, and wherein the advancing step comprises advancing the outer sleeve through the one or more layers of fascia before discontinuing advancing the outer sleeve.

40. The method of claim 39, wherein the outer sleeve extends distally beyond the carrier member when the carrier assembly is advanced, the outer sleeve sliding along an outer surface of the elongate member to guide the carrier assembly through the one or more layers of fascia.

41. The method of claim 32, wherein the opening through tissue communicates with a blood vessel, and wherein the deploying step comprises substantially sealing the opening from blood flow therethrough with the closure element.

42. The method of claim 41, wherein the elongate member comprises an introducer sheath, and wherein the method further comprises introducing one or more devices through the introducer sheath into the blood vessel to perform a procedure.

* * * * *